United States Patent
Schabron et al.

(10) Patent No.: US 7,487,662 B2
(45) Date of Patent: Feb. 10, 2009

(54) VOLATILE ORGANIC COMPOUND SENSOR SYSTEM

(75) Inventors: John F. Schabron, Laramie, WY (US); Joseph F. Rovani, Jr., Laramie, WY (US); Theresa M. Bomstad, Laramie, WY (US); Susan S. Sorini-Wong, Laramie, WY (US)

(73) Assignee: The University of Wyoming Research Corporation, Laramie, WY (US)

( * ) Notice: Subject to any disclaimer, the term of this patent is extended or adjusted under 35 U.S.C. 154(b) by 527 days.

(21) Appl. No.: 10/319,090

(22) Filed: Dec. 13, 2002

(65) Prior Publication Data

US 2004/0005715 A1    Jan. 8, 2004

Related U.S. Application Data

(60) Provisional application No. 60/405,638, filed on Aug. 23, 2002, provisional application No. 60/340,561, filed on Dec. 13, 2001.

(51) Int. Cl.
*G01D 18/00* (2006.01)
*G01N 21/00* (2006.01)
*G01N 7/00* (2006.01)
*G01N 27/00* (2006.01)

(52) U.S. Cl. .................. 73/23.2; 73/1.01; 73/1.02; 73/23.3; 436/43; 436/124; 436/126; 436/181; 422/83; 422/98

(58) Field of Classification Search .............. 73/1.01, 73/1.02, 23.2, 23.21, 23.3; 436/43, 124, 436/126, 181; 422/83, 98
See application file for complete search history.

(56) References Cited

U.S. PATENT DOCUMENTS

| | | |
|---|---|---|
| 3,742,475 A | 6/1973 | Liebermann et al. .... 340/237 R |
| 3,949,390 A | 4/1976 | Rayl et al. ................... 340/237 |
| 3,979,625 A | 9/1976 | Roberts ....................... 313/230 |
| 3,991,360 A | 11/1976 | Orth et al. ..................... 324/33 |
| 4,053,825 A | 10/1977 | Young ........................... 324/33 |
| 4,129,418 A | 12/1978 | Davis ........................... 422/98 |
| 4,151,641 A | 5/1979 | Mitoff .......................... 29/611 |
| 4,282,521 A | 8/1981 | Lieberman .................. 340/632 |
| 4,609,875 A | 9/1986 | Jeffers ......................... 324/455 |
| 4,666,672 A | 5/1987 | Miller et al. ................... 422/68 |
| 4,670,405 A | 6/1987 | Stetter et al. ................ 436/151 |
| RE32,552 E | 12/1987 | Liebermann et al. ........ 340/632 |

(Continued)

OTHER PUBLICATIONS

"Chemical Agents", Chemical and Biological Terrorism, National Academy Press, National Research Counsel, 1999, p. 113-131.
"Detection and Measurement of Chemical Agents", Chemical and Biological Terrorism, National Academy Press, National Research Counsel, 1999, p. 43-65, 227-263.
Adams, J.W., et al., 1997,"Development of Cone Penetrometer Electrochemical Sensor Probes for Chlorinated Solvents and Explosives", Field Analytical Methods for Hazardous Wastes and Toxic Chemicals, Air & Waste Management Association, pp. 667-670.

(Continued)

*Primary Examiner*—Brian J Sines
(74) *Attorney, Agent, or Firm*—Santangelo Law Offices, P.C.

(57) ABSTRACT

Generally, this invention relates to the development of field monitoring methodology for new substances and sensing chemical warfare agents (CWAs) and terrorist substances. It also relates to a portable test kit which may be utilized to measure concentrations of halogenated volatile organic compounds (VOCs) in the field. Specifically it relates to systems for reliably field sensing the potential presence of such items while also distinguishing them from other elements potentially present. It also relates to overall systems and processes for sensing, reacting, and responding to an indicated presence of such substance, including modifications of existing halogenated sensors and arrayed sensing systems and methods.

22 Claims, 18 Drawing Sheets

U.S. PATENT DOCUMENTS

| | | | | |
|---|---|---|---|---|
| 4,744,954 | A | 5/1988 | Campbell et al. | 422/98 |
| 4,771,006 | A | 9/1988 | Miller et al. | 436/126 |
| 4,831,332 | A | 5/1989 | Rudisill et al. | 324/455 |
| 4,839,143 | A | 6/1989 | Vora et al. | 422/98 |
| 4,879,546 | A | 11/1989 | Dunham et al. | 340/632 |
| 4,910,463 | A | 3/1990 | Williams, II et al. | 324/469 |
| 4,929,049 | A | 5/1990 | Le Goullon et al. | 350/96.29 |
| 5,012,197 | A | 4/1991 | Seiffert et al. | 324/696 |
| 5,104,513 | A | 4/1992 | Lee et al. | 204/425 |
| 5,106,756 | A | 4/1992 | Zaromb | 436/161 |
| 5,115,666 | A | 5/1992 | Williams | 73/19.1 |
| 5,153,520 | A | 10/1992 | Dumbeck | 324/469 |
| 5,157,333 | A | 10/1992 | Peacock et al. | 324/463 |
| 5,184,500 | A | 2/1993 | Krema et al. | 73/23.2 |
| 5,198,774 | A | 3/1993 | Williams, II et al. | 324/468 |
| 5,214,412 | A | 5/1993 | Gavlak et al. | 340/632 |
| 5,226,309 | A | 7/1993 | Stetter et al. | 73/31.06 |
| 5,260,036 | A | 11/1993 | Weigold | 422/186.3 |
| 5,284,569 | A | 2/1994 | Lee et al. | 204/425 |
| 5,293,130 | A | 3/1994 | Allman et al. | 324/469 |
| 5,301,537 | A | 4/1994 | Atkinson | 73/40 |
| 5,331,840 | A | 7/1994 | Williams | 73/19.1 |
| 5,347,223 | A | 9/1994 | Krcma et al. | 324/455 |
| 5,351,037 | A | 9/1994 | Martell et al. | 340/632 |
| 5,374,404 | A | 12/1994 | Weigold et al. | 422/186.3 |
| 5,397,552 | A | 3/1995 | Weigold et al. | 422/186.3 |
| 5,400,015 | A | 3/1995 | Liebermann | 340/642 |
| 5,444,435 | A | 8/1995 | Williams, II et al. | 340/632 |
| 5,448,905 | A | 9/1995 | Stetter et al. | 73/31.05 |
| 5,490,413 | A | 2/1996 | Atkinson | 73/40 |
| 5,561,065 | A | 10/1996 | Schabron | 436/28 |
| 5,601,184 | A | 2/1997 | Weigold | 204/157.15 |
| 5,707,595 | A | 1/1998 | Weigold et al. | 422/186.3 |
| 5,932,176 | A | 8/1999 | Yannopoulos et al. | 422/98 |
| 5,959,191 | A | 9/1999 | Lewis et al. | 73/31.05 |
| 5,976,883 | A | 11/1999 | Schabron | 436/28 |
| 5,979,054 | A | 11/1999 | Weigold et al. | 29/897.32 |
| 6,644,098 | B2 * | 11/2003 | Cardinale et al. | 73/25.01 |
| 6,703,840 | B2 * | 3/2004 | Cardinale | 324/535 |
| 7,074,365 | B1 * | 7/2006 | Shoaf | 422/82.08 |

OTHER PUBLICATIONS

Baron, Dirk, "Seience 360B-Introductinto Hydorlogic Systems", Dr. Dirk Baron, printed Dec. 11, 2002 3 pages; http://www.cs.csubak,edu/Geology/Faculty/Baron/SuppGWNotes-5.html.

Buttner, W.J., et al., 1995, "A Hand-Portable Instrument System for Real-Time Analysis of Chlorinated Organic Compound Contamination", Field Screening Methods for Hazardous Wastes and Toxic Chemicals, vol. 2, Air & Waste Management Association, 702-712.

Ewing, K.J., et al., 1995, "Fiber Optic Raman Volatile Organic Compound Sensor", Field Screening Methods for Hazardous Wastes and Toxic Chemicals, vol. 1, Air & Waste Management Association, pp. 364-371.

Frye, G.C., et al., 1995, "Above-Ground In-Situ Field Screening of VOCs Using a Portable Acoustic Wave Sensor (PAWS)", Field Screening Methods for Hazardous Wastes and Toxic Chemicals, vol. 2, Air & Waste Management Association, pp. 715-726.

Haas, J.W., et al., 1995, "Nonaqueous Phase Liquids: Searching for the Needle in the Haystack", Field Screening Methods for Hazardous Wastes and Toxic Chemicals, vol. 1, Air & Waste Management Association, pp. 443-449.

Hewitt, A.D. and Lukash, N.J., 1997, "Rapid Method for Estimating the Total Concentration of Volatile Organic Compounds in Solid Samples", Field Analytical Methods for Hazardous Wastes and Toxic Chemicals, Air & Waste Management Association, Pittsburgh, PA.

Hudak, R., Melby. J., Onisk, D., and Stave, J., 1995, Validation of an Immunoassay Field Screen for Trichloroethylene (TCE), Field Screening Methods for Hazardous Wastes and Toxic Chemicals, vol. 1, Conference Proceedings, Air & Waste Management Association, Pittsburgh, PA 101-108.

Linenberg, A. 1995, "On-Site Monitoring of Vinyl Chloride at Part Per Trillion Levels in Air", Field Screening Methods for Hazardous Wastes and Toxic Chemicals, vol. 1, Air & Waste Management Association, pp. 236-245.

Myers, K.F., et al., 1995, "Laboratory Evaluation of a Volatile Organic Compound Analysis System for the Site Characterization and Analysis Demonstration System", Field Screening Methods for Hazardous Wastes and Toxic Chemicals, vol. 1, Air & Waste Management Association, pp. 177-184.

Penrose, William, 1993, "Chlorinated hydrocarbon vpor sensor technologies include PID, FID, helium plasma arc, solid state sensor", EPA, pp. 3.

Plumb Jr., R.H., 1992, "The Importance of Volatile Organic Compounds as a Disposal Site Monitoring Parameter", in Lesage, S. and R.E. Jackson, eds., Groundwater Contamination and Analysis at Hazardous Waste Sites. Marcel Dekker, New York, NY, pp. 173-197.

Rossabi, J., et al., 1993, "In Situ, Subsurface Monitoring of Vapor-Phase TCE using Fiber Optics", Proceedings of the 1993 USEPA/A &WMA, International Symposium on Field Screening Methods for Hazardous Wastes and Toxic Chemicals, Air & Waste Management Association, pp. 1165-1175.

Schabron, J.F. and J.F. Rovani, Jr., 1997, "Practical Deviations from Henry's Law for Water/Air Partitioning of Volatile Organic Compounds", Proceedings of the 1997 USEPA/A&WMA International Symposium on Field Screening Methods for Hazardous Wastes and Toxic Chemicals, Air & Waste Management Association, pp. 417-426.

Schabron, J.F.,et al., 1996, Down Hole Photoionization Detection of Volatile Organic Stach, J., J. Flachowsky, M. Brodacki, and H.R. Doring, 1995, Field Screening for Volatile Organochlorine Compounds Using Ion Mobility Spectrometry, Field Screening Methods for Hazardous Wastes and Toxic Chemicals, vol. 2, Air & Waste Management Association, pp. 1046-1050.

Stach, J., J. Flachowsky, M. Brodacki, and H.R. Doring, 1995, Field Screening for Volatile Organochlorine Compounds Using Ion Mobility Spectrometry, Field Screening Methods for Hazardous Wastes and Toxic Chemicals, vol. 2, Air & Waste Management Association, pp. 1046-1050.

TIF Instruments, Inc, "Refrigerant Leak Detectors", 1 page.

TIF Instruments, Inc., Oct. 29, 2001, "Leak Detectors", 1 page.

Walt, D.R, 1998, Fiber Optic Imaging Sensors, Accounts of Chemical Research, 31, 267-278.

Yokogawa Coporation of America, "Refrigerant Leak Detector", 1 page.

Yokogawa Coporation of America, 2000, "Refrigerant Monitor Specifications", 1 page.

U.S. Nonprovisional "Soil Extraction Stirring System", U.S. Appl. No. 09/558,979, filed Apr. 27, 2000, 20 pages and 3 drawings.

U.S. Appl. No. 60/340,561, filed Dec. 13, 2001, entitled "Halogenated Volatile Organic Compound Screening and Measurement", 18 pages and 1 drawing.

U.S. Appl. No. 60/405,638, filed Aug. 23, 2002 entitled "System To Selectively Detect The Presence Of Chemical Warfare Agents", 12 pages and 2 drawings.

International Preliminary Examination Report; PCT/US02/40082; Sep. 28, 2004, 5 pages.

* cited by examiner

GA Tabun

GB Sarin

GD Soman

VX

AC Hydrogen Cyanide

CK Cyanogen Chloride

Chlorine

$Cl_2$

CG Phosgene

HD Sulfur Mustard

Nitrogen Mustard

Lewisite

$Cl-CH=CH-AsCl_2$
(cis-and trans)

SARIN

PHOSGENE

SULFUR MUSTARD

US 7,487,662 B2

VOLATILE ORGANIC COMPOUND SENSOR SYSTEM

CROSS-REFERENCES TO RELATED APPLICATIONS

This application claims the benefit of U.S. Provisional Application No. 60/340,561, filed Dec. 13, 2001, entitled "Halogenated Volatile Organic Compound Screening and Measurement" and U.S. Provisional Application No. 60/405, 638; filed Aug. 23, 2002 entitled "System To Selectively Detect The Presence Of Chemical Warfare Agents", both hereby incorporated by reference.

ACKNOWLEDGMENT OF GOVERNMENT SUPPORT

This invention was made with federal government support under Cooperative Agreement Nos. DE-FC26-98FT40322 awarded by the U.S. Department of Energy. The federal government may have certain rights in this invention.

TECHNICAL FIELD

Generally, this invention relates to the development of field screening methodology for new substances and sensing chemical warfare agents (CWAs) and terrorist substances. It also relates to a portable test kit which may be utilized to measure concentrations of halogenated volatile organic compounds (VOCs) in the field. Specifically it relates to systems for reliably field sensing the potential presence of such items while also distinguishing them from other elements potentially present. It also relates to overall systems and processes for sensing, reacting, and responding to an indicated presence of such substances.

BACKGROUND

Contamination by halogenated volatile organic compounds (VOCs) may be considered to be a widespread problem at U.S. Department of Energy (DOE) and military sites. It also has environmental ramifications. Compounds such as carbon tetrachloride, trichloroethylene, tetrachloroethylene, etc. may commonly be referred to as dense nonaqueous phase liquids (DNAPLs). These compounds may have been used extensively in degreasing and equipment cleaning operations in the past, with disposal practices that led to their release into the ground, and thus may be considered the most significant organic contaminants in groundwater associated with disposal sites (Plumb 1992).

For measurement of concentrations or amounts, the photoionizaton detector (PID) may be among the most common VOC field measurement tool in use today. A typical PID lamp energy may be 10.6 electron volts (eV), which can be sufficient for ionizing compounds containing double bonds. However, halogenated compounds without double bonds such as carbon tetrachloride or methylene chloride may require an energy of 11.7 eV for ionization (Table 5) (Schabron et al. 1996). This may only be accomplished with a PID equipped with a lithium fluoride window, which may be considered to have a short lifetime due to the solubility of lithium fluoride in water. Also, a PID may not be considered to be selective for halogenated compounds. Many other compound types may be detected also. Field screening of soils with a PID probe may involve placing a soil sample in a plastic bag or a glass jar, sealing the bag or covering the jar with aluminum foil, then inserting the PID probe tip through the foil (Hewitt and Lukash 1997).

In an unrelated field, leak testing of refrigerants is often conducted in situations warranting isolated testing events. In such situations, heated diode and corona discharge sensors are used merely as alarm sensors to detect leaks of refrigerants from air conditioners, freezers, and refrigerators, since both heated diode and corona discharge sensors are selective to the presence of halogens or carbon-halogen bonds. These test procedures, however, have been viewed as not applicable to quantitative analysis.

In situations calling for quantitative analysis of VOCs, PID's are used. Besides the aforementioned problems, though, such hand-held PID detectors may also suffer from the disadvantage in that they may not be able to discriminate between halogenated and non-halogenated species (Table 5). A more detailed analysis which may also allow for some speciation involves a portable gas chromatograph (Myers et al. 1995, Linenberg 1995). This is a relatively expensive type of device, however, skilled operators are usually required, as is the flow of a chemically inert carrier gas. Immunoassay kits may also allow for rapid field analysis (Hudak et al. 1995). This approach may require temperature control and critical timing for the several steps involved.

Several novel approaches have been proposed for surface or down-hole screening of halogenated VOCs in the field. One approach may use refractive index attenuation on coated optical fibers (Le Goullon and Goswami 1990). Another technology may utilize a chemical reaction in a basic media to form a color in the presence of trichloroethylene (Rossabi et al. 1993). Yet, another probe may use a heated $LaF_2$ doped element heated to 600° C. to measure volatile chlorine containing compounds (Buttner et al. 1995). A synthetic nose consisting of an array of different chemicals which may give different optical response to various volatile analytes has been proposed (Walt 1998). Other approaches may also include Raman spectroscopy (Ewing et al. 1995, Haas et al. 1995), electrochemical cells (Adams et al. 1997), acoustic wave devices (Frye et al. 1995), and ion mobility spectrometry (Stach et al. 1995). The above devices certainly may all contribute some progress towards the problem of monitoring for some of the VOC indicator compounds at various levels, but none meet user needs across the full spectrum.

Thus, there exists a need for a new type of simple field monitor (such as a portable field kit) which is selective to halogenated VOCs, field-worthy (portable, not overly complex to operate, not requiring extensive (or perhaps any) on-site lab facilities, and enabling field monitoring, including in situ sensing or operating of the monitor), and does not require skilled operation (meaning it is easy to operate by anyone with only minimal instruction). HVC (halogenated volatile compound) sensing (or more generally sense operating) upon merely positioning a sensor in an area of interest an activating a switch(es) is a desirable feature. Sensing as used herein may refer to sensing for the presence of a chemical and/or determining the concentration of a chemical. Monitoring may be characterized by any type of chemical group (halogenated VC, e.g), or by purpose (environmental, groundwater, or soil, as but a few examples). Monitoring includes sensing to assess the presence of a chemical functional group and/or sensing to determine the concentration of a chemical functional group.

The presence of chemical warfare agents (CWAs) and terrorist substances is one of increasing concern. Hand-held and portable sensor systems are commercially available for the detection of various chemicals in vapor form in ambient air. These sensors typically use a detector system based on photoionization, corona-discharge, heated diode, thermal conductivity, ion mobility spectrometry, ion capture, or other technology. Many of the sensor systems incorporate an air pump to flow sampled air past the detector, while other sensors use air diffusion. Generally, they do not, however, offer adequate differentiation to be employed in the highly sensitive security setting. For example, if only a halogen-selective detector device were used for the detection of halogen-containing chemical warfare agents (CWAs) such as sarin, soman, phosgene, and sulfur mustard, the inability to differentiate between these chemicals and other more common chemicals such as refrigerants, dry cleaning solvents, and degreasing solvents might cause a false alarm in a public setting. This could cause panic and hysteria.

Current state-of-the-art sensor technology suffers to some degree from a lack of applicability of individual sensors to a variety of chemical vapors. Often, individual detector systems are either too specific or too broad in scope for measuring a suite of chemical vapors. A detector that is too specific, such as corona-discharge, is limited to detection of a unique chemical structure and cannot evaluate chemicals of different classes. A detector that is too broad-based, such as thermal conductivity, responds to almost any vapor without regards to chemical specificity. Systems capable of identifying individual compounds, such as mass spectrometers, can often be too expensive for widespread deployment.

DISCLOSURE OF INVENTION

An important aspect of the initial data collection for the present invention includes the use of commercially available heated diode and corona discharge leak detectors which can be obtained from the manufacturers and modified or utilized as necessary to provide a signal related to VOC concentration. In addition, efforts may include the evaluation and potential calibration of sensor response using carbon tetrachloride and tetrachloroethylene (perchloroethylene, PCE) since these compounds represent halogenated VOCs, with and without double bonds. Using this approach, the response characteristics may be determined for the VOCs directly in headspace in Tedlar bag containers. Quantitation limits for carbon tetrachloride in the air were estimated to be 1 ug/L (0.2 ppmv) by using the modified heated diode detector and 50 ug/L (10 ppmv) by using the modified corona discharge detector. Detector operation was not modified to provide additional sensitivity although this could be possible as well. An operative sensitivity might be improved if a signal to noise ration is improved by minimizing the size of the apparatus, and/or by arranging the apparatus in a sensor array that includes at least one additional halogenated volatile compound sensor apparatus (perhaps forming a parallel sensor array), as but two examples. Potential interferences from volatile hydrocarbons, such as toluene, heptane, and the like were also evaluated. In one embodiment these interferences may be concluded as not significantly affecting the response from either such detector. Another important aspect of the detection process may be the effect of humidity. The heated diode detector may not respond significantly to humidity while the corona discharge detector may give a slight response to humidity, which may then be zeroed out as background. The results of these efforts indicate the value that both devices may have for analytical method development work toward one goal of the present invention of developing a portable test kit for screening and measuring halogenated VOCs in the field. These results may also suggest the use of the sensors in the present invention to merely detect the presence of halogen-containing volatile chemical warfare agents (or halogenated volatile compound chemical warfare agent, which may be a halogenated volatile organic compound chemical warfare agent) in air at low levels. Halogen-containing chemical warfare agents include sarin, phosgene, and mustard gas, etc., (see FIG. 28).

One embodiment of the present invention may be a field portable kit based on heated diode or corona discharge monitor technology for screening for halogenated VOCs in the field. Another embodiment may be the application of this technology to quantitative analysis. Of commercial importance is the fact that two widely used commercially available refrigerant leak detectors can be modified and used as both field screening and monitoring devices for new types of halogenated VOCs and as a quantitative tool. Indeed, the objectives of the present invention include using commercially available refrigerant leak detectors as continuously operable field screening and monitoring devices and as measurement devices.

Heated diode leak monitors were manufactured by Yokogawa and now by Bacharac, Inc., Newnan, Ga. These operate on 12 volts at less than 1 amp. Corona discharge leak monitors are commercially available from American Test Products Inc., Mirimar, Fla. These are the so-called TIF sensors may involve high impedance circuits operating at about 1,600 volts at the detector tip. Both types of sensor systems are said to be capable of detecting leaks of down to approximately 0.1 to 0.5 ounce of refrigerant per year. Both of these detectors are sold as alarm monitors without a quantitative or a digital readout. In one embodiment, the present invention may involve modification of these types of commercially available heated diode and corona discharge monitors to provide quantitative or semi-quantitative determination and display (digital readout or otherwise, steady-signal readout or otherwise) of halogenated VOCs in the field. Other monitors, commercially available or not, that also are responsive to halogens or carbon-halogen bonds may also be modified to sense in the field the presence of halogenated VOCs in a manner similar to that described herein. Results to date suggest the possibility of using the above-specified (and other) sensors to detect halogen-containing volatile chemical warfare agents in air at low levels. Additional initial experiments performed with carbon tetrachloride and tetrachloroethylene in air and soil may provide a method by which to define product specification and establish the concept discussed in the present invention which may then assist in creating the new analytical methods of detection.

In one embodiment, the present invention involves field test kits and the measurement of VOCs and may be an important aspect in developing new environmental monitoring applications for heated diode or corona discharge-based leak detectors, and the like, and for selectively screening for new substances or measuring new and more traditional halogenated VOCs in the field. The devices could perhaps be used with the plastic bag or aluminum foil covered jar sampling method described above for soil samples; they may involve utilization of the headspace above a contained water. Such use may involve water sparging to rapidly release volatile organic compounds entrained or dissolved in the water (which includes freshwater, seawater, brackish water, groundwater, as but a few different types). Alternatively, the devices could be used as a portable cost effective means of detecting volatile halogen-containing chemical warfare agents such as sarin, phosgene, mustard gas, or chlorine, and the like in air. The XP-1 has an air fan in the body of the unit, but it does not work well. Another important inventive aspect of the system involves retrofitting onto a corona discharge sensor a pump that provides a controlled and variable flow of air across the sensor and enhances sensitivity, accuracy and field operability of the device or apparatus.

Yet another important aspect of another embodiment of the present invention may involve the impact of the partitioning of VOCs between air and water as a function of temperature and the concentration of VOC species in water (Schabron et al. 1996, Schabron and Rovani 1997). Headspace may be either in the air above the water table in a well, or a headspace artificially created below the surface of the water by a membrane or other device. An important aspect in the principles of operation for a headspace device may be attributed to Henry's law, which states that the partial pressure $P_i$, or concentration of a volatile component in the headspace is proportional to its concentration in the aqueous solution $C_i$:

$$P_i = H_i \times C_i$$

where $H_i$ is the Henry's law constant for component i. The assumptions in using this approach for determining VOCs are that they have not exceeded their solubility in water, and that they partition into the headspace according to Henry's law. For example, $H_i$ relates the mg/L vapor parts per million (ppmv) level in the headspace to the mg/L concentration in water. Thus, the vapor concentration of toluene in equilibrium with a 1 mg/L aqueous toluene solution at 25° C.(77° F.) is 69 ppmv. By measuring the ppmv levels of volatile organics in the headspace above aqueous solutions of these materials, field screening personnel often assume that the aqueous level can be established. $H_i$ is only defined at infinite dilution. The actual partitioning may vary significantly with total VOC concentration in the water and with temperature. Headspace may only be used to estimate water concentration if the appropriate corrections are made.

The present invention may be expected to support the development of many new commercial products which may provide a cost-effective means to rapidly screen for halogenated VOCs or chemical warfare agents in the field. An important aspect of the present invention involves taking existing refrigerant detector alarm monitors, and with slight hardware modification and comprehensive analytical method development work launching them into a new commercial application with significant utility to the environmental industry. In spite of the availability of such devices, this new use is inventive, as is the method of application associated with this new use, because such uses were often viewed as impossible by those in the field. An important and ultimate goal of the present invention is to develop a field portable kit based on heated diode or corona discharge monitor technology that may be used to screen for halogenated VOCs or chemical warfare agents in the field. Such measurement or screening may be enhanced by the present invention's modification of available halogenated VOC sensors to provide numerical or digital readout indicative of presence or concentrations of halogenated VOC's.

Another important aspect of the present invention is that the detector system be able to work in an environment of varying and often high relative humidity. Response characteristics and background levels may be derived experimentally at different relative humidities. Potential interferences from aliphatic or aromatic hydrocarbons may be considered minimal. The detector even demonstrates a significant selectivity to halogenated VOCs in the presence of non-halogenated VOCs.

MODES FOR CARRYING OUT THE INVENTION

Figure 1:
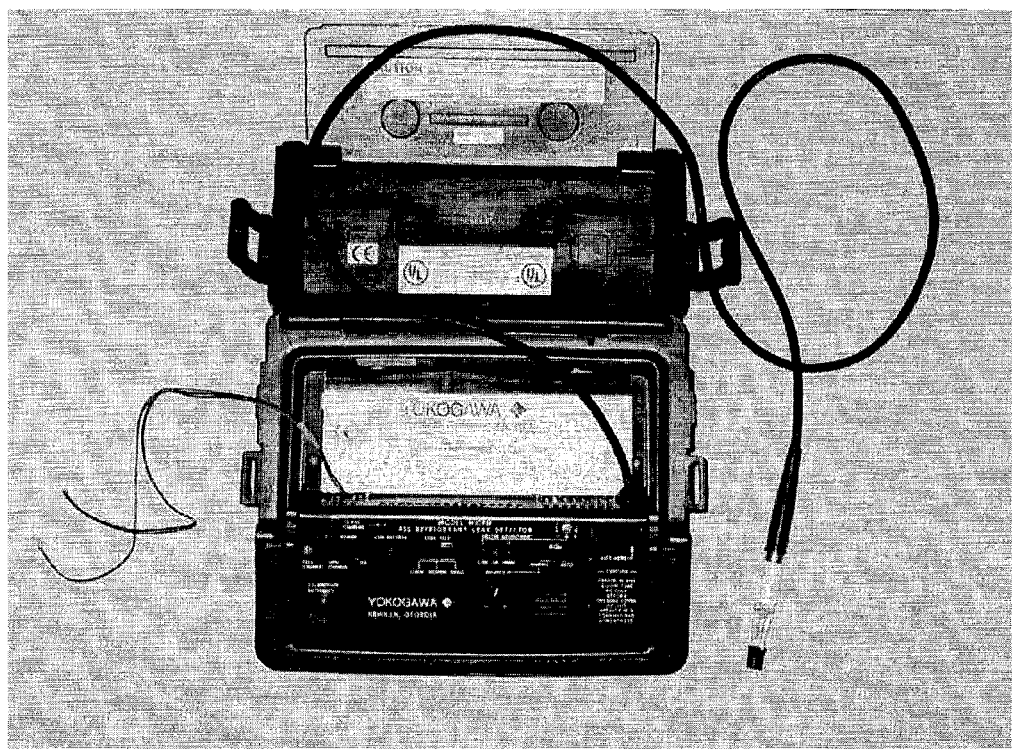
FIG. 1 shows a Yokogawa H-10PM Heated Diode Leak Detector.

Preferred embodiments of the invention are described herein by presenting the setup of sensor-based examples and the conclusions drawn therefrom.

EXAMPLE DETAILS

Chemicals

Carbon tetrachloride and tetrachloroethylene (perchloroethylene, PCE) were 99.9% ACS reagent grade from Aldrich. Heptane and toluene were reagent grade from VWR. Certified standard solutions of carbon tetrachloride and tetrachloroethylene in methanol at 200 ug/mL were from Supelco.

Heated Diode Leak Detector

The heated diode sensor was a model H-10PM refrigerant leak detector from Yokogowa Corp, Newnan, Ga. An internal sampling pump draws air through a heated diode sensor which operates between temperatures ranging from about 600-1000° C. The sensor selectively interacts with halogens present in the volatile organic compounds that it encounters. This is based on positive ion emission technology, wherein halogens cause an ionized current to flow. The device has an on-board sampling pump which operates at two different flow rates, which control the device's sensitivity. The low flow rate provides the most sensitivity, while the highest flow rate provides the least sensitivity. Sensitivity can also be controlled by adjusting the temperature of the diode heater, with a higher temperature providing greater sensitivity. There is an audio alarm which produces a chirping sound when volatile halogenated compounds are present. Since there is no visual readout, the sensor device was modified by attaching a voltmeter to the electrical output of the sensor so that the voltmeter is responsive to the electrical output. This was accomplished by connecting wires to the output of the signal processing amplifier in the device by CF Electronics, Laramie, WY to provide an output signal which ranges from 0-15 V. The output was connected to a Linseis L200E strip chart recorder. The voltmeter and any other devices necessary to generate a numerical output from the sensor may be referred to as a numerical output provision element. It provides a numerical output (or reading) that is indicative of a concentration of a chemical such as a halogenated volatile compound. Upon such provision the operator of the apparatus obtains or receives a numerical output or reading, perhaps in real time or more generally in short time. The new device may be referred to a halogenated volatile compound sensor apparatus. This halogenated volatile compound may be a halogenated volatile organic compound, as the term halogenated volatile compound in the specification may include halogenated volatile organic compound. Inventive methods related to this sensor (and the corona discharge sensor discussed below) may be referred to as hologenated volatile compound sensing methods Corona Discharge Leak Detector The corona discharge device was a TIF model XP-1 refrigerant leak detector from ATP, Inc., Mirimar, Fla. The mechanical sampling pump to deliver sampled air to the sensor tip did not work well, and thus, detection of chemical vapor is by diffusion only. Note that, as used herein, establishing a sensor in a certain area does not require that the entire sensor be put in that area, but merely that the sensor tip (or other sensitive part of the sensor) be established (or placed or positioned or located, e.g.) in that area. The sensor tip was repeatedly waved or swept over objects, areas, substances or gases to be tested, in an attempt to physically contact the sensor tip with chemical vapors. In order to effectively estimate the location of a chemical leak, the sensor tip was relocated every few seconds to an area void of any chemical vapors, to "re-zero" the sensor. The sensor operates at a potential difference of 1,500 to 2,000 VDC. A discharge current of about 10 microamperes is decreased by the presence of halogen containing VOCs. This perturbation of current is difficult to interpret directly, and the manufacturer has developed a digital signal processing algorithm to convert the change in current or voltage into an audible alarm and a visual readout consisting of a series of light emitting diodes (LEDs) on the front panel which relate to the concentration of contaminant. To provide a stable readout, the device was fitted with a "T" fitting at the sensor tip and a personal sampling pump usually employed for chemical vapor air monitoring in personal hygiene applications to provide an even sample flow across the sensor tip. The pump was configured to pull sampled air past the sensor tip upstream from the pump. The sensor tip was fitted into a low void-volume stainless steel "T" fitting carefully machined to eliminate leakage and to provide consistent air flow past the sensor tip. A TIF model H-10A detector with an air fan in the sensor wand was used also.

The TIF units produce both an audible beep and a light readout when it detects chemical vapors. For the XP-1, the color and number of LED lights is proportional to the amount of chemical vapor detected. For the H-10, the frequency of an audible beep is proportional to the amount of chemical vapor detected. As originally configured, the beeping sound cannot be used to estimate nor quantitate amounts or concentrations of chemical vapors. However, the LED readout can be employed in somewhat simple fashion to gauge the approximate concentration of chemical vapors. One approach may be visually indicative in nature and may involve, for example, a LED readout of three colors and six lights produces a net range of 0 through 18 lights for each of seven sensitivity levels. The most two sensitive levels (levels 6 and 7) exhibited significant background noise, and thus they were not used in the current work. Other visual indicators that indicate the presence and, possibly, the level of concentration of the volatile vapor may be employed. Also, an audible indicator(s) may be used in addition to, or instead of, a visual indicator(s).

A halogenated volatile compound sensor apparatus may be created by modifying a corona discharge sensor by electrically attaching a frequency meter to the H-10A.

The frequency meter and any other devices necessary to generate a numerical output from the sensor may be referred to as a numerical output provision element. It provides a numerical output that is indicative of a concentration of a chemical such as a halogenated volatile compound.

Gas Chromatography

The gas chromatograph (GC) used for the determination of VOCs was a Hewlett-Packard (Agilent Technologies) 5890A equipped with an electron capture detector. The column was a J&W DB-624, 30 m×0.53 mm×30 urn film thickness, operated isothermally at 50° C. (167° F.). The GC results were not affected by the presence or absence of water vapor in the samples.

Tedlar Bag Experiments

Six calibration standards in methanol were prepared from the certified standard solutions in methanol. Volumes of 1 uL of the six calibration standards were injected into the GC, and a linear calibration range was determined.

Saturated headspace vapors of carbon tetrachloride were obtained by pipetting 20 mL of carbon tetrachloride into a 175 mL glass gas-sampling apparatus containing a silicone septum. After overnight liquid/vapor equilibration, the ambient laboratory air temperature was recorded, and uL quantities of saturated headspace vapor were withdrawn through the septum using a gas-tight syringe. These were injected into septum-ported 1 liter and 5 liter Tedlar bags containing dry breathing-quality air introduced from a gas cylinder. Vapor equilibration by diffusion was found to take only a few minutes, and uL quantities of air containing carbon tetrachloride vapor were withdrawn by gas-tight syringe and injected into the GC for analysis to determine ug carbon tetrachloride/L air, and ppmv concentrations.

The probe tip of the Yokogawa heated diode unit was inserted into the Tedlar bag port, after quickly removing the septum. The heated diode sensor responses in volts were recorded using the strip chart recorder wired to the amplified signal outputs. Signal responses from 0 through 15 volts were recorded for the small, medium, and large settings, using the unit's auto mode. Between individual Tedlar bag readings, the unit was re-zeroed using a Tedlar bag blank containing dry air only.

The probe tip of the TIF corona discharge unit was inserted into the bottom port of a carefully machined 316 stainless steel "T" fitting. A 2" piece of PTFE tubing was used to connect one of the top ports to a personal sampling pump, and a second 2" piece of PTFE tubing was used to connect the top port to the Tedlar bag. The corona discharge responses were recorded by counting the number of LED lights illuminated at sensitivity levels 3, 4, and 5. Between individual Tedlar bag readings, the unit was re-zeroed in a Tedlar bag blank with dry air only.

Similar to the dry air environment experiments described above, carbon tetrachloride vapor concentration data were obtained in saturated water vapor environments, using mL quantities of water pipetted into the Tedlar bags. After overnight water liquid/water vapor equilibration at ambient laboratory temperatures, the carbon tetrachloride concentrations were determined by GC, and the responses were determined for the Yokogawa and TIF units. Between individual Tedlar bag readings, the units were re-zeroed using a Tedlar bag blank containing dry air only. Readings from a Tedlar bag containing saturated water vapor alone were obtained also.

The units were also evaluated for their responses to carbon tetrachloride vapor with toluene and n-heptane vapors. Saturated headspace vapors of toluene and n-heptane were prepared in glass gas-sampling apparatuses as described above. Headspace vapors of equal volume amounts to saturated carbon tetrachloride vapors, 10-fold volume amounts, and 100-fold volume amounts were prepared for toluene and n-heptane. Between individual Tedlar bag readings, the units were re-zeroed using a Tedlar bag blank containing dry air only. Readings from Tedlar bags containing various amounts of toluene or n-heptane vapors alone were obtained also.

Results and Discussion

Sensor Response

Sensor response was evaluated by isolating variables such as VOC type, and potential interferences. Responses were evaluated for two distinctly different types of halogenated VOCs, one without double bonds (carbon tetrachloride), and one with a double bond (tetrachloroethylene). The response characteristics were determined for the VOCs directly in headspace, without soil, in Tedlar bags. Quantitation limits were estimated based on a signal to noise ratio of 10 for the Yokogowa heated diode sensor, and at the appearance of three lighted LEDs for the TIF discharge sensor. Potential interferences from volatile hydrocarbons, such as toluene and heptane were evaluated. The effect of humidity was studied also.

a. Heated Diode Sensor

The Yokogawa unit has three sensitivity settings (small, medium, large) which alter the amplified signal by changing both the pump flow rate to the detector and the temperature of the diode, and by attenuation of the electronic signal. Experiments conducted using carbon tetrachloride vapors in sealed air sampling bags containing dry air have shown that the quantitation limit of the unit is approximately 0.2 vapor parts per million (ppmv). Using the most sensitive "small" setting, the lower value of 0.2 ppmv was obtained by strip chart recorder using a signal to noise ratio of 10. Using the least sensitive "large" setting, an upper value of 35 ppmv is in a region where the detector response has become non-linear. The precise value of the upper working range had not been determined at that time because 35 ppmv is at the upper calibration range of the gas chromatograph used to quantitate the exact concentration of carbon tetrachloride in the bags. Additional experiments can be performed to establish the full dynamic response range, of course.

It has been demonstrated in the laboratory that the presence of saturated water vapor in air samples is not chemically detected in any significant fashion. Moreover, saturated water vapor does not significantly alter the response profile of the detector to carbon tetrachloride. Similarly, the presence of toluene and n-heptane are not chemically detected in significant fashion, and do not significantly alter the response curve profile of the detector to carbon tetrachloride which was determined from 0.2-35 ppmv. Toluene and n-heptane vapors were tested for each point on the response curve at three levels of saturated vapor headspace injected into the Tedlar bags relative to carbon tetrachloride: in equal volumes to carbon tetrachloride, at 10-fold vapor volumes to carbon tetrachloride, and at 100-fold vapor volumes to carbon tetrachloride.

b. Corona Discharge Sensor

The TIF unit has seven sensitivity settings which electronically attenuate the LED lights. In this example, sensitivity level 7 and to a lesser degree, 6, could not be used reliably because they appear to give irreproducible results that bounced and jumped excessively. Experiments conducted using carbon tetrachloride vapors in sealed Tedlar air sampling bags containing dry air have shown that the quantitation limit of the unit is approximately 10 ppmv. Using the sensitivity level 5 setting, the lower value of 10 ppmv was obtained using the least number of lights that yield a reliable quantitation, which is three lights. Levels 3, 4, and 5 were used to explore the working range of the unit. The upper working range of the TIF unit had not yet been determined because 35 ppmv is at the upper calibration range of the gas chromatograph used to quantitate the exact concentration of carbon tetrachloride in the bags. Additional experiments can be performed to establish the full dynamic response range, of course.

The TIF unit gives a chemical response to saturated water vapor in air, which is equivalent to about 20 ppmv of carbon tetrachloride. The response curve of carbon tetrachloride vapor in combination with saturated water vapor is thus the combined sum of the two individual responses. However, it was demonstrated in the laboratory that if the TIF unit is re-zeroed in a saturated water vapor environment, the response curve of carbon tetrachloride vapor in combination with saturated water vapor is roughly equivalent to that of carbon tetrachloride in dry air.

The presence of toluene and n-heptane are not chemically detected in significant fashion, and do not significantly alter the response curve profile of the detector to carbon tetrachloride which was determined from 10-35 ppmv. Toluene and n-heptane vapors were tested for each point on the response curve at three levels of saturated vapor headspace injected into the Tedlar bags relative to carbon tetrachloride: in equal volumes to carbon tetrachloride, at 10-fold vapor volumes to carbon tetrachloride, and at 100-fold vapor volumes to carbon tetrachloride.

Experiment Conclusions

Commercially available heated diode and corona discharge leak detectors were obtained from the manufacturers. These were modified to provide readouts which correspond to the concentration of halogenated VOCs in air. Sensor response was evaluated with carbon tetrachloride. The response characteristics were determined for the VOCs directly in headspace, without soil, in containers such as in Tedlar bags. Quantitation limits were estimated. Potential interferences from volatile hydrocarbons, such as toluene and heptane were evaluated. The effect of humidity was studied also.

TABLE 5

PID Detectability for Volatile Organic Compounds

| Compound | PID Detectability | |
|---|---|---|
| | 10.6 eV | 11.7 eV |
| Dichloromethane (Methylene chloride) | N | Y |
| Trichloroethylene | Y | Y |
| Tetrachloroethylene | Y | Y |
| trans-1,2-Dichloroethylene | Y | Y |

TABLE 5-continued

PID Detectability for Volatile Organic Compounds

| Compound | PID Detectability | |
|---|---|---|
| | 10.6 eV | 11.7 eV |
| Trichloromethane (Chloroform) | N | Y |
| 1,1-Dichloroethane | N | Y |
| 1,1-Dichloroethylene | Y | Y |
| 1,1,1-Trichloroethane | N | Y |
| Toluene | Y | Y |
| 1,2-Dichloroethane | N | Y |
| Benzene | Y | Y |
| o-Xylene | Y | Y |
| Ethylbenzene | Y | Y |
| Vinyl chloride | Y | Y |
| Carbon tetrachloride | N | Y |
| Chlorobenzene | Y | Y |
| p-Dichlorobenzene | Y | Y |
| Naphthalene | Y | Y |

Figure 28:
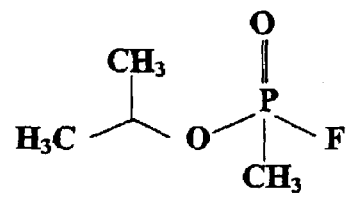
FIG. 28 is a representation of examples of Halogen containing volatile organic compounds.
Figure 28:
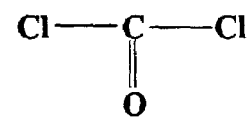
Figure 28:
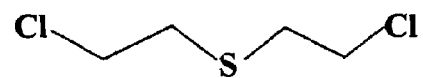

The present invention involves a screening methodology and a portable test kit to measure and distinguish substances such as halogenated volatile organic compounds (VOCs) in the field. One embodiment involves the use of heated diode and corona discharge sensors such as are commonly used as alarm sensors to detect leaks of refrigerants from air conditioners, freezers, and refrigerators. These are capable of detecting the presence of halogens or carbon-halogen bonds. Further, commercially available and inexpensive heated diode and corona discharge leak detectors can be adapted to provide a numerical signal related to VOC concentration as well as to detect specific CMAs. As one example, halogen-containing chemical warfare agents including sarin, phosgene, and mustard gas (as depicted in FIG. 28) may be individually detected and reacted to.

The invention may also involve an air sampling train of multiple sensors constructed using a variety of chemical detection sensor technologies in a chemical vapor sensor array apparatus. It may include existing detectors may modified to maximize their sensitivity, or unmodified existing sensors. Further, multiple sensors may be sequenced for a desired result. It is important to understand that, as used herein, the phrase "at least one other sensor" is characteristic of not only a different type of sensor, but also of a different, discrete sensor (i.e. the at least one other sensor can be the same as the referenced sensor). Non-destructive chemical detectors may be configured upstream from destructive detectors in airflow channels which may even separately condition the air to be sensed. Air may be sampled using precise pumps or mass flow controllers. Construction may be in a wall-mounted box for passive sampling, in a portable field unit, or in other arrangements. Initial and periodic calibration of the detector array or sensor array (or chemical vapor sensor array) may be accommodated, and subsequent detector signals or sense outputs could even be collected by a multivariate analysis element such as a central computing device employing pre-programmed logic schemes to interpret results, thereby said multivariate analysis element may operate on sense outputs to generate (perhaps in real time) a sensible indication as to the concentration of a chemical functional group. The term "sensible indication as to concentration of a chemical functional group" (regardless of what type of chemical functional group it is), is intended to refer to not only an indication as to the actual concentration of the group (which may be merely one type of chemical), but also to an indication of merely whether that group exists (i.e., its presence). The multivariate analysis element could function to provide information as to the presence and/or concentration of a chemical functional group. As one example, a positive signal by both photoionization and heated diode sensors may be interpreted as indicative of a halogenated chemical with a double bond; a positive signal by thermal conductivity could indicate a relatively high level of aliphatic hydrocarbon; signal ratio data, perhaps previously stored in a unit's microprocessor could be applied to interpret the various detector signals, and possibly to identify an individual compound such as a volatile chemical warfare agent, or halogenated volatile chemical warfare agent. As such, one goal of the invention would be to provide a cost-effective means to analyze chemical vapors in air for a variety of purposes, including environmental, security, and defense applications. Importantly, the term environmental monitoring is a term of art (i.e., environment here has a different scope than surroundings), and generally refers to, as but a few examples, groundwater monitoring (for contaminants, e.g.), soil monitoring and air monitoring. Testing for refrigerant leaks near a device using refrigerant is not considered environmental monitoring. The term environmental area of interest is also accorded such a meaning.

In an embodiment of the invention using an air sampling train of single or multiple sensors, there may be a configuration of cells or tubes or fibers containing materials that may selectively prevent certain selected classes of chemicals from passing through. These may permit separate conditioning for individual sensors. This could allow for additional degrees of selectivity in such devices. In one embodiment, the system may differentiate between classes of chemicals by using selective adsorption (via a selective adsorption element), absorption (via a selective absorption element), or reaction (via a selective reaction element) of a particular class of chemicals by passing them through a cell, tube, filter, or fiber or other selective chemical group removal element comprising materials which may prevent their passage. There may be a sensor at the inlet and another sensor at the outlet of the tube and the two may be combined to permit an appropriate determination. Chemicals that do not adsorb or absorb or react with the cell contents may pass through and be detected by both sensors. Chemicals that do not pass through may be detected by only the one sensor at the inlet of the tube. Such are merely a few ways in which a chemical functional group (which may include one chemical type) can be sensed (either to assess its presence and/or to determine its concentration). Such a chemical functional group may be further characterized as a volatile compound functional group, or a halogenated functional group, or a halogenated chemical warfare agent group, as but a few examples.

For example, sarin reacts readily with water. One configuration of a sensor device could be a halogen-selective sensor placed at the inlet of a cell containing water, either bound or as a liquid. A second identical sensor could be placed at the cell outlet. The air containing sarin would be passed across the first sensor, through the cell (or sarin removal element, in this case), and across the second sensor. Sarin would be detected by the first sensor, but not the second. Halogen-containing refrigerants such as the Freons or their replacements, or solvent vapors such as methylene chloride or tetrachloroethylene might pass through the wet cell and thus they would be detected by both sensors permitting a differentiation. Either levels of response, types of response, or any other factor may be utilized to permit an appropriate determination or differentiation. Environmentally sensitive substances that may detected or distinguished may include: Dichloromethane (Methylene chloride), Trichloroethylene, Tetrachloroethylene, trans-1,2-Dichloroethene, Trichloromethane (Chloroform), 1,1-Dichloroethane, 1,1-Dichloroethene, 1,1,1-Trichloroethane, Toluene, 1,2-Dichloroethane, Benzene, o-Xylene, Ethylbenzene, Vinyl chloride, Carbon tetrachloride, Chlorobenzene, p-Dichlorobenzene, Naphthalene, and others.

Sensor response relative to carbon tetrachloride and tetrachloroethylene (perchloroethylene, PCE) which represent halogenated VOCs with and without double bonds may also be used. The detectors may be configured to give a different response for PCE relative to carbon tetrachloride. Qualitative information leading to possible compound or compound type identification can also be obtained by using multiple sensors together and taking a ratio of their signals. Environmental analysis applications may also be available. Configuration may also be selected so that potential interferences from volatile hydrocarbons, such as toluene and heptane may not significantly affect the response from one or more detectors. The effect of humidity may also be included and detectors may be selected to either not respond significantly to humidity or perhaps even for any response to humidity to be zeroed out as background either upon setup, upon start up, or by automatic operation.

Sensors may also be chosen to detect halogen-containing volatile chemical warfare agents in air at low levels. Halogen-containing chemical warfare agents (CWA) including at least sarin, phosgene, and mustard gas may be specified by the design or software. An ability to differentiate between halogenated CWAs and halogenated VOCs such as halogenated dry cleaning or degreasing solvents or refrigerants may be included. This could avoid false alarms, and in a civilian setting, panic and mass hysteria.

For cost savings, modified refrigerant leak detectors may be used. With the addition of more detector technologies, the device may even be adaptable to detect a variety of non-halogenated VOCs and CWAs and to even identify individual compounds or compound classes, or to rule out specific interferences that might give a signal with one of the sensors either on initial design, or as more frequent occurrences arise. A detector array containing both heated diode and corona discharge halogenated-selective sensors configured with other sensor types such as thermal conductivity, photoionization, hydrocarbon detectors, and others can be used. In addition, the use of selective removal of analytes between sensors using adsorption, absorption, or reaction can be applied to gain additional degrees of selectivity. These can be combined with any sensor combination.

The system may provide a cost-effective means to rapidly screen for halogenated VOCs or chemical warfare agents in the field. Existing refrigerant detector alarm monitors with slight hardware modification and analytical method adaptation may be used for specific utility. Of course a variety of configurations are possible as well as a variety of detectors. Another goal of the invention is to provide a cost-effective means to differentiate between species, such as halogenated chemical warfare agents, possible in air and other halogenated compounds such as refrigerants, dry cleaning solvents, and degreasing solvents. Yet another goal is to provide for the selective detection of chemical vapors such as in air or otherwise.

In an array system, computer software for multi-variate analysis may be used. This could be based on commercially available or custom-written software. Potential system capabilities or features for different embodiments include, but are not limited to:

providing a wall-mounted, passive device, perhaps like a smoke detector in appearance;
providing potentially an integrated, hand-held device (such as a handheld chemical vapor sensor array apparatus);
utilizing an array of sensors;
utilizing an array of commercially available sensors modified to detect and identify volatile CWAs perhaps released in air;
providing analysis results within seconds, or more generally a short time (which, as used herein, refers to any one of less than 1 second, less than 3 seconds, less than 5 seconds, less than 10 seconds, less than 30 seconds, or less than that of any existing apparatus) (real time as used herein refers to less than one second);
providing a systems with a varied CWA target list including but not limited to GA, GB, GD, AC, CK, CG, chlorine, nitrogen and sulfur mustard, and in non-volatile sensor systems, perhaps VX;
providing and deploying a system designed or positioned for use in public areas such as subways, airport terminals, sports arenas, malls, etc.;
providing a system which may be battery powered, perhaps as a backup to regular AC power for high reliability; and
providing a system capable of being interfaced with facility CWA defense systems perhaps to automatically trigger an official reaction/notification a release of an appropriate counter agent or chemical treatment (perhaps as simple as a release of water such as in a spray fire extinguisher system [water destroys some agents such as GB and GD]) or, more generally, a response which is designed to mitigate or to render the CWA harmless, and/or to automatically elicit any other appropriate security response.
obtaining at least two volatile compound sensors; arranging sensors in an array so that each may sense a gas of interest (such as air in a headspace above water or soil, e.g.); initiating operation of the sensors (as by activating a switch); and obtaining a sensible indication relative to a concentration of a volatile compound functional group As should be understood, the system may be configured using any combination or a great variety of sensor techniques. Detectors include a large variety of possibilities. One instrument adaptable for field (or in-field) screening for VOCs is a hand-held photoionization detection (PID) instrument. While PID detectors suffer from a disadvantage in that they cannot discriminate between halogenated and non-halogenated species the above designs may be applied to overcome deficiencies. Another type of portable detector is the portable gas chromatograph. Again, although when used alone, this type of detector requires skilled operators, it may be adapted for easy use. Existing refrigerant detectors and alarm monitors may be used perhaps with only slight hardware modification. Heated diode and corona discharge monitor technology may be utilized. Heated diode leak monitors such as are available from Bacharach, Inc. in Newnan, Ga. may be applied operating on 12 volts at less than 1 amp. A refrigerant leak detector such as a TIF model XP-1 from ATP, Inc. may be used. This is a corona discharge device with a discharge current of about 10 microamperes which is decreased by the presence of halogen-containing VOCs. A TIF H-10A can be utilized and operated on 115 V. Other corona discharge leak monitors such as are available from TIF Instruments, Inc., Mirimar, Fla. may be applied. Detectors may include high-impedance circuits operating at about 1,500 to 2,000 volts at the detector tip. Immunoassay kits can be used and existing designs may be perhaps adapted for rapid field analysis. Even though the immunoassay approach can require temperature control and critical timing and a sequence of steps such may be automated. Surface and down-hole screening of halogenated VOCs in the field can be used. Refractive index attenuation on coated optical fibers can be used. Chemical reaction in a basic media to form a color in the presence of trichloroethylene is possible. A radio frequency-induced helium plasma optical emission spectrometer can be used. Probes using a $LaF_2$-doped element heated to about 600° C. (1,112° F.) can be used. A synthetic nose consisting of an array of different chemicals that give different optical responses to various volatile analytes may be applied. Raman spectroscopy, detectors for volatile DNAPLs, detectors to measure aromatic rings by ultraviolet light absorption, detectors which ionize compounds containing double bonds, detectors using a lithium fluoride window, electrochemical cells, acoustic wave devices, and ion mobility spectrometry are each possible. These and others types of detectors are detailed in several of the articles and other documents incorporated by reference in this application. For example, one heated diode sensor could be a device such as applied in model H-10PM refrigerant leak detector from Yokogowa Corp, Newnan, Ga. Devices as shown in U.S. Pat. Nos. 3,979,625 and 3,991,360 and 4,151, 641 (each hereby incorporated by reference) may be employed. A corona discharge device such as TIF model H-10A refrigerant leak detector from Advanced Test Products, Inc., Mirimar, Fla. or as shown in U.S. Pat. Nos. RE32, 552 and 3,742,475 (each hereby incorporated by reference) could be included. Other devices which could be used in particular embodiments include but are not limited to: a photoionization detector, a combustible hydrocarbon sensor, a thermal conductivity detector, an electrochemical cell, a quartz crystal microbalance, a surface acoustic wave device, an optical spectrometer (ultraviolet, visible, infrared, fluorescence, phosphorescence, raman, or photoacoustic), an ultrasonic sensor, a heat capacity transducer, other gas-selective sensors. Key here is that with the teachings of this invention and a knowledge of the agents of interest, specific reactions may be achieved and assured.

The detector system also may be designed to work in an environment of varying and often high relative humidity. Response characteristics and background levels may be evaluated at different relative humidities and may be accommodated by the system. Potential interferences from aliphatic or aromatic hydrocarbons may be designed to be minimal. The system may also be designed to demonstrate a significant selectivity to halogenated VOCs in the presence of non-halogenated VOCs.

A digital readout or other indication may be included. Sensible indication (which may be real time in at least one embodiment) as used herein refers to an indication that can be sensed by a human or perhaps an apparatus. In other embodiments, an audible alarm and a visual readout consisting of a series of lighted diodes on the front panel that relate to the concentration of contaminant may be included. An audible beep and an LED readout can be used with or without the frequency of the beep, and the color and/or number of LED lights being designed to be proportional to the amount of chemical vapor detected. An LED readout of three colors and six lights can be configured to produce a net signal range of 0 through 18 lights for each of a variety of sensitivity levels. Such levels may also electronically attenuate the signal from the detector. A flashing neon light and an audible popping signal (perhaps personalized to prevent hysteria) that increases in frequency as higher amounts of agent are sensed can be included. Frequencies from about 1-300 Hz can be used and any aspect can even be recorded for historical, comparison, or verification purposes. Outputs which enable the user to "home-in" on the location of a chemical source (perhaps using a chemical functional group source location element responsive to the sensors) can be included. A steady-signal readout can be used and can be configured to provide quantitative or semiquantitative determination of halogenated VOCs or other substances in the field.

Figure 29:
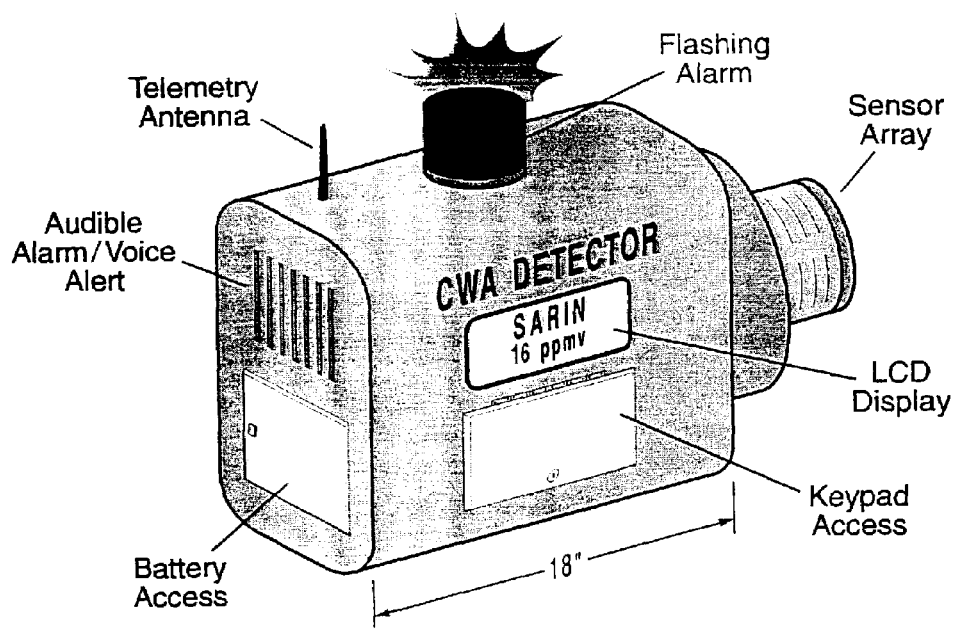
FIG. 29 is a device which could be deployed as a wall-mounted unit such as a smoke detector

As shown in FIG. 29, for CWA detection, a device could be deployed as a wall-mounted unit such as a smoke detector. Positive identification could cause an alarm to sound or send a signal to a security office. Possibly hand portable versions of these devices could be developed also. Applications could include CWA detection and other applications for VOC detection including environmental screening and emergency response. The system may be designed as an integrated, self contained device. It may include a small fan within the body of the unit to pull sampled air past the appropriate detector(s) at a constant flow perhaps using a low-void volume stainless steel fitting perhaps carefully machined to eliminate leakage and void volumes, and to provide consistent air flow. Air flows of about 150 mL/min may be used.

As can be easily understood from the foregoing, the basic concepts of the present invention may be embodied in a variety of ways. It involves both detection techniques as well as devices to accomplish the appropriate detection. In this application, the detection techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which will be included in a full patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for the full patent application. It should be understood that such language changes and broad claiming will be accomplished when the applicant later (filed by the required deadline) seeks a patent filing based on this provisional filing. This full patent application may seek examination of as broad a base of claims as deemed within the applicant's right and will be designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sensor" should be understood to encompass disclosure of the act of "sensing"—whether explicitly discussed or not—and, conversely, were there effectively disclosure of the act of "sensing", such a disclosure should be understood to encompass disclosure of a "sensor" and even a "means for sensing." Such changes and alternative terms are to be understood to be explicitly included in the description.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement or reference statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to claim at least: i) each of the detection devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and apparatuses substantially as described hereinbefore and with reference to any of the accompanying examples, x) the various combinations and permutations of each of the elements disclosed, xi) processes performed with the aid of or on a computer or computational device as described throughout the above discussion, xii) a programmable apparatus as described throughout the above discussion, xiii) a computer readable memory encoded with data to direct a computer comprising means or elements which function as described throughout the above discussion, xiv) a computer configured as herein disclosed and described, xv) individual or combined subroutines and programs as herein disclosed and described, xvi) the related methods disclosed and described, xvii) similar, equivalent, and even implicit variations of each of these systems and methods, xviii) those alternative designs which accomplish each of the functions shown as are disclosed and described, xix) those alternative designs and methods which accomplish each of the functions shown as are implicit to accomplish that which is disclosed and described, xx) each feature, component, and step shown as separate and independent inventions, xxi) the various combinations and permutations of each of the above, xxii) each potentially dependent claim or concept as a dependency on each and every one of the independent claims or concepts presented. In this regard it should be understood that for practical reasons and so as to avoid adding potentially hundreds of claims, the applicant may eventually present claims with initial dependencies only. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any acts of law, statutes, regulations, or rules mentioned in this application for patent; or patents, publications, or other references mentioned in this application for patent, are each hereby incorporated by reference. Specifically, U.S. patent application Ser. No. 60/340,561, filed Dec. 13, 2001 and U.S. patent application Ser. No. 60/405,638; filed Aug. 23, 2002 are hereby incorporated by reference including any figures or attachments. Any Exhibits mentioned or included within this application, specifically Exhibits 1 and 2, are hereby incorporated by reference, as are any tables.

In drafting any claims at any time whether in this provisional application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Exhibit 1

WRI-02-R013

FIELD SCREENING FOR HALOGENATED VOLATILE ORGANIC COMPOUNDS

Topical Report

By
John F. Schabron
Joseph F. Rovani, Jr.
Theresa M. Bomstad

June 2002

Work Performed Under Cooperative Agreement
DE-FC26-98FT40322  Task 3.8

For
U.S. Department of Energy
Office of Fossil Energy
National Energy Technology Laboratory
Morgantown, West Virginia By
Western Research Institute
Laramie, Wyoming

ACKNOWLEDGMENTS

Funding for this study was provided by the U.S. Department of Energy under Cooperative Agreement DE-FC26-98FT40322. The authors would like to acknowledge Tony Munari for preparing the figures.

DISCLAIMER

This report was prepared as an account of work sponsored by an agency of the United States Government. Neither the United States Government nor any agencies thereof, nor any of its employees, makes any warranty, expressed or implied, or assumes any legal liability or responsibility for the accuracy, completeness, or usefulness of any information, apparatus, product, or process disclosed, or represents that its use would not infringe on privately owned rights. Reference herein to any specific commercial product, process, or service by trade name, trademark, manufacturer, or otherwise does not necessarily constitute or imply its endorsement, recommendation, or favoring by the United States Government or any agency thereof. The views and opinions of authors expressed herein do not necessarily state or reflect those of the United States Government or any agency thereof.

ABSTRACT

Western Research Institute (WRI) initiated exploratory work towards the development of new field screening methodology and a test kit to measure halogenated volatile organic compounds (VOCs) in the field. Heated diode and corona discharge sensors are commonly used to detect leaks of refrigerants from air conditioners, freezers, and refrigerators. They are both selective to the presence of carbon-halogen bonds. Commercially available heated diode and corona discharge leak detectors were procured and evaluated for halogenated VOC response. The units were modified to provide a digital readout of signal related to VOC concentration. Sensor response was evaluated with carbon tetrachloride and tetrachloroethylene (perchloroethylene, PCE), which represent halogenated VOCs with and without double bonds. The response characteristics were determined for the VOCs directly in headspace in Tedlar bag containers. Quantitation limits in air were estimated. Potential interferences from volatile hydrocarbons, such as toluene and heptane, were evaluated. The effect of humidity was studied also. The performance of the new devices was evaluated in the laboratory by spiking soil samples and monitoring headspace for halogenated VOCs. A draft concept of the steps for a new analytical method was outlined. The results of the first year effort show that both devices show potential utility for future analytical method development work towards the goal of developing a portable test kit for screening halogenated VOCs in the field.

TABLE OF CONTENTS

<div align="right"><u>Page</u></div>

LIST OF TABLES ..................................................................................................................... v

LIST OF FIGURES ................................................................................................................... vi

EXECUTIVE SUMMARY ....................................................................................................... viii OBJECTIVES ............................................................................................................................. 1

INTRODUCTION ...................................................................................................................... 1
    Halogenated Volatile Organic Compounds ........................................................................ 1
    Background ......................................................................................................................... 1
    Current Approaches ............................................................................................................ 4
    New Methodology .............................................................................................................. 4

EXPERIMENTAL DETAILS ................................................................................................... 5 ...... Chemicals
    Heated Diode Leak Detector .............................................................................................. 5
    Corona Discharge Leak Detectors ...................................................................................... 5
    Gas Chromatography .......................................................................................................... 5
    Tedlar Bag Experiments ..................................................................................................... 5
    Water Vapor Experiments .................................................................................................. 6
    Toluene and n-Heptane Vapor Experiments ...................................................................... 7
    Soil Spiking ......................................................................................................................... 7
    Sensor Interchangeability ................................................................................................... 7

RESULTS AND DISCUSSION ................................................................................................ 8
    Sensor Response ................................................................................................................. 8
    Yokogawa Heated Diode Sensor ........................................................................................ 8
    TIF Corona Discharge Sensors ......................................................................................... 11
    Elements of a New Analytical Method ............................................................................ 17
CONCLUSIONS ....................................................................................................................... 17

REFERENCES ................................................................................................................. 18

LIST OF TABLES

| Table | | Page |
|---|---|---|
| 1. | PID Detectability for Volatile Organic Compounds | 2 |
| 2. | Yokogawa H-10PM Relative Response of Carbon Tetrachloride and Tetrachloroethylene | 11 |
| 3. | TIF H-10A Relative Response of Carbon Tetrachloride and Tetrachloroethylene | 16 |

LIST OF FIGURES

| Figure | | Page |
|---|---|---|
| 1. | Yokogawa H-10PM Heated Diode Leak Detector | 22 |
| 2. | Response Profile of Yokogawa H-10PM | 23 |
| 3. | Expanded View of Lower Working Range of Yokogawa H-10PM | 23 |
| 4. | Yokogawa H-10PM Response Profile in Saturated Water Vapor Environment | 24 |
| 5. | Yokogawa H-10PM Response to Toluene Vapor | 24 |
| 6. | Yokogawa H-10PM Response Profile in Toluene Vapor Environment | 25 |
| 7. | Yokogawa H-10PM Response to n-Heptane Vapor | 25 |
| 8. | Yokogawa H-10PM Response in n-Heptane Vapor Environment | 26 |
| 9. | Yokogawa H-10PM Sensor Interchangeability | 26 |
| 10. | Yokogawa H-10PM Sensor Comparison with Temperature Adjustment | 27 |
| 11. | Yokogawa H-10PM Soil Spiking Results | 27 |
| 12. | TIF XP-1 Leak Detector with Auxiliary Du Pont P200A Personal Sampling Pump | 28 |
| 13. | Response Profile of TIF XP-1 | 29 |
| 14. | Expanded View of Lower Working Range of TIF XP-1 | 29 |
| 15. | TIF XP-1 Response in Saturated Water Vapor Environment | 30 |
| 16. | TIF XP-1 Response in Toluene Vapor Environment | 30 |
| 17. | TIF XP-1 Response Profile in n-Heptane Vapor Environment | 31 |
| 18. | TIF XP-1 Soil Spiking Results | 31 |

LIST OF FIGURES (continued)

| Figure | | Page |
|---|---|---|
| 19. | TIF XP-1 Sensitivity Level 3, Sensor Interchangeability | 32 |

20. TIF XP-1 Sensitivity Level 4, Sensor Interchangeability ...................................... 32

21. TIF XP-1 Sensitivity Level 5, Sensor Interchangeability ...................................... 33

22. TIF H-10A Leak Detector .................................................................................... 34

23. Response Profile of TIF H-10A ............................................................................ 35

24. TIF H-10A Sensor Interchangeability .................................................................. 35

EXECUTIVE SUMMARY

Western Research Institute (WRI) initiated exploratory work towards the development of new field screening methodology and a test kit to measure halogenated volatile organic compounds (VOCs) in the field. Heated diode and corona discharge sensors are commonly used to detect leaks of refrigerants from air conditioners, freezers, and refrigerators. They are both selective to the presence of carbon-halogen bonds. Commercially available heated diode and corona discharge leak detectors were evaluated for halogenated VOC response. The units were modified as necessary to provide a numerical readout of signal related to VOC concentration. Sensor response was evaluated with carbon tetrachloride and tetrachloroethylene (perchloroethylene, PCE), which represent halogenated VOCs with and without double bonds. The response characteristics were determined for the VOCs directly in headspace in Tedlar bag containers. Detection limits in air were estimated. Potential interferences from volatile hydrocarbons, such as toluene and heptane, were evaluated. The effect of humidity was studied also. The performance of the new devices was evaluated in the laboratory by spiking soil samples and monitoring headspace for halogenated VOCs. A draft concept of the steps for a new analytical method was outlined. A summary of accomplishments from the current FY 01 effort is listed below.

- Commercially available heated diode and corona discharge leak detectors were obtained from the manufacturers. These were modified as required to provide readouts that correspond to the concentration of halogenated VOCs in air.

- Sensor response was evaluated by isolating variables such as VOC type and potential interferences. Responses were evaluated in air for two distinctly different types of halogenated VOCs; one without double bonds, carbon tetrachloride; and one with a double bond, tetrachloroethylene. The response characteristics were determined for the VOCs directly in headspace, without soil, in containers such as Tedlar bags. Quantitation limits (S/N=10) were estimated to be 0.2 vppm for the heated diode detector and 10 vppm for the corona discharge detectors. Potential interferences from volatile hydrocarbons, such as toluene and heptane, were evaluated and found to be minimal. The effect of humidity was studied also. Humidity did not affect the response profiles of either detector to carbon tetrachloride. Minimal backgrounds due to saturated humidity could easily be zeroed out.

- The performance of the new devices was evaluated in the laboratory by spiking soil samples and monitoring headspace for halogenated VOCs. A draft concept of the steps required to develop new analytical methods with these devices was prepared.

OBJECTIVES

The ultimate goal of the multiyear effort is to develop a field portable kit based on heated diode or corona discharge monitor technology for screening halogenated volatile organic compounds (VOCs) in the field. The objectives of the first-year effort were to obtain two widely used commercially available refrigerant leak detectors and evaluate them for possible use as field screening and monitoring devices for halogenated VOCs. Heated diode leak monitors are commercially available from Yokogawa U.S. Corporation in Newnan, Georgia. These operate on 12 or 120 volts at less than 1 amp. Corona discharge leak monitors are commercially available from American Test Products Inc., Miami, Florida. These involve high-impedance circuits operating at about 1,600 volts at the detector tip. Both types of sensor systems are said to be able to detect leaks of down to about 0.1 to 0.5 ounce of refrigerant per year. Both of these detectors are sold as alarm monitors without a digital readout. Western Research Institute (WRI) modified both of these types of commercially available monitors to provide quantitative or semiquantitative determination of halogenated VOCs in the field. Initial experiments were performed with carbon tetrachloride and tetrachloroethylene in air and soil. The concept of a new analytical method was established.

INTRODUCTION

Halogenated Volatile Organic Compounds

Contamination by halogenated VOCs is a widespread problem at U.S. Department of Energy (DOE) and military sites. Compounds such as carbon tetrachloride, trichloroethylene, tetrachloroethylene, etc. are commonly referred to as dense nonaqueous phase liquids (DNAPLs). These were used extensively in degreasing and equipment cleaning operations in the past, with disposal practices that led to their release into the ground. Some are still in use as degreasing solvents in the petroleum refining and other industries (U.S. DOE 1998). Studies of data from 500 sites show that VOCs are the most significant organic contaminants in groundwater associated with disposal sites (Plumb 1992). These represented 75% of events involving organic contamination in both CERCLA, RCRA, and municipal landfill sites. Plumb (1992) found an identical mathematical relationship between VOCs and organic priority pollutants detected. He suggested that monitoring for VOCs be used as an early warning system for excursions to indicate the need for more extensive laboratory analysis for organics, and that statistical considerations show that this will work correctly more than 90% of the time. The top 18 VOCs of interest are listed in Table 1 (Plumb 1991). A similar, but not identical, list was developed for sites in Germany (Kerndorff et al. 1992).

Background

A new screening method was developed by WRI for determining the presence of fuels containing aromatic components, particularly diesel fuel in soils (Sorini and Schabron 1997, Schabron et al. 1995). It has been approved by the American Society for Testing and Materials (ASTM) as Method D-5831, Standard Test Method for Screening Fuels in Soils (ASTM 2000).

Table 1. PID Detectability for Volatile Organic Compounds

| Compound | PID Detectability | |
|---|---|---|
| | 10.6eV | 11.7eV |
| Dichloromethane (Methylene chloride) | N | Y |
| Trichloroethylene | Y | Y |
| Tetrachloroethylene | Y | Y |
| trans-1,2-Dichloroethene | Y | Y |
| Trichloromethane (Chloroform) | N | Y |
| 1,1-Dichloroethane | N | Y |
| 1,1-Dichloroethene | Y | Y |
| 1,1,1-Trichloroethane | N | Y |
| Toluene | Y | Y |
| 1,2-Dichloroethane | N | Y |
| Benzene | Y | Y |
| o-Xylene | Y | Y |
| Ethylbenzene | Y | Y |
| Vinyl chloride | Y | Y |
| Carbon tetrachloride | N | Y |
| Chlorobenzene | Y | Y |
| p-Dichlorobenzene | Y | Y |
| Naphthalene | Y | Y |

A new *Diesel Dog*® Soil Test Kit is being commercialized by WRI to perform the method in the field. Questions frequently arise as to whether the kit can measure volatile DNAPLs, since this is a problem encountered by many state agencies and environmental engineering firms. The method employed by the *Diesel Dog* kits measures aromatic rings by ultraviolet light absorption, thus it is not amenable to halogenated VOCs. A need for a simple portable field kit and method to detect volatile DNAPLs is apparent. Over the last decade, research at WRI included work with photoionization detection (PID) with various types of VOCs in soil and water. PID is the most common VOC field screening tool in use today. A typical PID lamp energy is 10.6 electron volts (eV), which is sufficient for ionizing compounds containing double bonds. However, halogenated compounds without double bonds, such as carbon tetrachloride or methylene chloride, require an energy of 11.7 eV for ionization (Table 1) (Driscoll and Becker 1979). This can only be accomplished with a PID equipped with a lithium fluoride window, which has a short lifetime due to the solubility of lithium fluoride in water. Also, a PID is not selective for halogenated compounds. Many other compound types are detected also. Field screening with a PID probe involves placing a soil sample in a plastic bag or a glass jar, sealing the bag or covering the jar with aluminum foil, then inserting the PID probe tip through the foil (Hewitt and Lukash 1997).

There exists a need for a new type of simple field monitor that is selective to halogenated VOCs. Heated diode and corona discharge sensors are commonly used as alarm monitors to detect leaks of refrigerants from air conditioners, freezers, and refrigerators. Both are selective to the presence of carbon-halogen bonds. The expertise that has been developed at WRI in the area of field test kits and the measurement of VOCs is being applied to developing a new environmental monitoring application for heated diode or corona discharge-based leak detectors. This is expected to result in a new method and test kit for selectively screening for halogenated VOCs in the field. The devices could be used with the plastic bag or foil-covered jar sampling procedures described above for soil samples, or to measure the headspace above water.

Recent research at WRI involved studies of the partitioning of VOCs between air and water as a function of temperature and the concentration of VOC species in water (Schabron et al. 1996, Schabron and Rovani 1997). Headspace can be either in the air above the water table in a well, or artificially created below the surface of the water by a membrane or other device. The principle of operation for a headspace device is Henry's law, which states that the partial pressure $P_i$, or concentration of a volatile component in the headspace, is proportional to its concentration in the aqueous solution $C_i$:

$$P_i = H_i \times C_i \tag{1}$$

where $H_i$ is the Henry's law constant for component i. The assumptions in using this approach for determining VOCs are that they have not exceeded their solubility in water, and that they partition into the headspace according to Henry's law. For example, $H_i$ relates the mg/L vapor parts per million (vppm) level in the headspace to the mg/L concentration in water. Thus, the vapor concentration of toluene in equilibrium with a 1-mg/L aqueous toluene solution at 25 °C (77 °F) is 69 vppm. By measuring the vppm of volatile organics in the headspace above aqueous solutions, field screening personnel often assume that the aqueous level can be established. $H_i$ is only defined at infinite dilution and the partitioning varies significantly with total VOC water concentration and with temperature (Schabron and Rovani 1997). Headspace can only be used to estimate water concentration if the appropriate corrections can be made.

Current Approaches

The most common instruments used for field screening for VOCs are hand-held PID-based instruments. PID detectors suffer from a disadvantage in that they cannot discriminate between halogenated and non-halogenated species (Table 1). A more detailed analysis that also allows for some speciation involves a portable gas chromatograph (Myers et al. 1995, Linenberg 1995). Skilled operators are required. Immunoassay kits allow for rapid field analysis (Hudak et al. 1995). This approach requires temperature control and critical timing for the several steps involved.

Several novel approaches have been proposed for surface or down-hole screening of halogenated VOCs in the field (Schabron et al. 1991). One approach uses refractive index attenuation on coated optical fibers (Le Goullon and Goswami 1990, Oxenford et al. 1989). Another technology uses a chemical reaction in a basic media to form a color in the presence of trichloroethylene (Milanovich et al. 1994, 1986). A radio frequency-induced helium plasma optical emission spectrometer has been designed to measure some volatile chlorinated compounds (Olsen et al. 1989). Another probe uses a $LaF_2$-doped element heated to 600 °C (1,112 °F) to measure volatile chlorine-containing compounds (Buttner et al. 1995, Stetter and Cao 1990). A synthetic nose consisting of an array of different chemicals that give different optical response to various volatile analytes has been proposed (Walt 1998). Other approaches include Raman spectroscopy (Ewing et al. 1995, Haas et al. 1995), electrochemical cells (Adams et al. 1997), acoustic wave devices (Frye et al. 1995), and ion mobility spectrometry (Stach et al. 1995). The above devices all contribute some progress towards the problem of monitoring for some of the VOC indicator compounds at various levels. These are not commercially available.

The detector system also must be able to work in an environment of varying and often high relative humidity. Response characteristics and background levels must be evaluated at different relative humidities. Potential interferences from aliphatic or aromatic hydrocarbons must be minimal. The detector must demonstrate a significant selectivity to halogenated VOCs in the presence of non-halogenated VOCs.

New Methodology

The current work is expected to lead to the development of new commercial products that will provide a cost-effective means to rapidly screen for halogenated VOCs in the field. The work involves taking existing refrigerant detector alarm monitors, and with slight hardware modification and comprehensive analytical method development, launching them into a new commercial application with significant utility to the environmental industry. The ultimate goal of the multiyear effort is to develop a field portable kit based on heated diode or corona discharge monitor technology for screening for halogenated VOCs in the field. The objectives of the proposed work are to obtain two widely used commercially available refrigerant leak detectors and evaluate them for possible use as field screening and monitoring devices for halogenated VOCs. Heated diode leak monitors are commercially available from Yokogawa U.S. Corporation in Newnan, Georgia. These operate on 12 volts at less than 1 amp. Corona discharge leak monitors are commercially available from TIF Instruments, Inc., Miami, Florida. These involve high-impedance circuits operating at about 1,600 volts at the detector tip. Both types of sensor systems are said to be able to detect leaks of down to about 0.1 to 0.5 ounce of refrigerant per year. Both of these detectors are sold as alarm monitors without a digital readout.

EXPERIMENTAL DETAILS

Chemicals

Carbon tetrachloride and tetrachloroethylene (perchloroethylene, PCE) were 99% + from Aldrich. Heptane and toluene were reagent grade from commercially available sources.

Heated Diode Leak Detector

The heated diode sensor was a model H-10PM refrigerant leak detector from Yokogawa Corporation, Newnan, Georgia.

Corona Discharge Leak Detectors

The corona discharge devices were the TIF model XP-1 and the TIF H-10A refrigerant leak detectors from Advanced Test Products, Inc., Miami, Florida.

Gas Chromatography

The gas chromatography (GC) analyses were performed with a Hewlett-Packard 5890A GC equipped with an electron capture detector. The column was a J&W DB-624 30 m x 0.53 mm i.d. x 3 micron film thickness. Six GC calibration standards for each VOC were prepared from certified standard solutions in methanol from Supelco. Volume amounts of 1 uL of each of the six calibration standards were injected into the GC, and a linear calibration range consisting of area response vs. pg of VOC injected was determined on a daily basis.

Tedlar Bag Experiments

Saturated headspace vapors of carbon tetrachloride and tetrachloroethylene were obtained by pipetting 20 mL of liquid-phase VOC into a 175-mL, glass, gas-sampling apparatus containing a PTFE-lined silicone septum. After overnight liquid/vapor equilibration, the ambient laboratory air temperature was recorded, and various uL quantities of saturated headspace vapor were withdrawn through the septum using a gas-tight syringe. These were injected into septum-ported 1-L and 5-L Tedlar bags containing dry breathing-quality grade air introduced from a gas cylinder. Vapor equilibration by diffusion was found to take only a few minutes, and various uL quantities of air containing VOC vapor were withdrawn from the Tedlar bags by gas-tight syringes and injected into the GC for analysis to determine vppm concentrations.

The probe tip of the Yokogawa H-10PM was inserted into the Tedlar bag port, after quickly removing the septum. The on-board air pump was used to draw sampled air into the heated diode chamber. The heated diode sensor response in volts was recorded using the strip chart recorder wired to the amplified signal outputs. Signal responses ranging from 0 through 15 volts were recorded for the small, medium, and large settings, using the unit's auto mode. Between individual Tedlar bag readings, the unit was rezeroed using a bag blank containing dry air only.

The probe tip of the TIF XP-1 was inserted into the bottom port of a carefully machined 316 stainless steel "T" fitting. A two-inch piece of PTFE tubing was used to connect one of the top ports to a Du Pont P200A personal sampling pump set at a flow rate of 150 mL/min. A second two-inch piece of PTFE tubing was used to connect the other top port of the "T" to the Tedlar bag port, after quickly removing the septum. The corona discharge responses were recorded by counting the number of LED lights illuminated at sensitivity levels 1 through 5. Between individual Tedlar bag readings, the unit was rezeroed using a bag blank containing dry air only.

The probe tip of the TIF H-10A was inserted directly in the Tedlar bag port, and a small fan located just downstream from the corona discharge sensor pulled sampled air past the sensor. The frequency of the audible signal response was recorded using a multimeter set to the frequency (Hz) mode. Frequency responses were obtained at three sensitivity levels, using blank background settings at 1, 2, and 4 Hz. Between individual Tedlar bag readings, the unit was rezeroed using a Tedlar bag blank containing dry air only.

Water Vapor Experiments

The H-10PM and XP-1 were tested for their response to saturated water vapor at ambient temperatures. 1 mL of water was pipetted into a 1-L Tedlar bag, and the bag was manually shaken. After overnight liquid/vapor equilibration, the units were set to zero with dry air and evaluated for their response to 100% relative humidity.

In similar fashion to the dry air environment experiments described above, carbon tetrachloride vapor responses were obtained in saturated water vapor environments, using 1 mL of water pipetted into a 1-L Tedlar bag, and 5 mL of water pipetted into a 5-L bag. After overnight liquid/vapor equilibration at ambient laboratory temperatures, carbon tetrachloride vapor concentrations in the presence of 100% relative humidity were determined by GC, and the responses were obtained for the heated diode H-10PM and the corona discharge XP-1 devices. Between individual Tedlar bag readings, the units were rezeroed using a Tedlar bag blank containing dry air only. A second set of responses was obtained in which the units were rezeroed using a Tedlar bag blank containing saturated water vapor.

Toluene and n-Heptane Vapor Experiments

The H-10PM and XP-1 were tested for their response to toluene and n-heptane vapors. Saturated headspace vapors of toluene and n-heptane were prepared in glass, gas-sampling apparatuses as described above. Various volumes of saturated headspace vapor were withdrawn and injected into Tedlar bags containing dry air, and the units were evaluated for their response.

The H-10PM and XP-1 were then evaluated for their response to carbon tetrachloride vapor in the presence of toluene vapor and n-heptane vapor environments. For these studies, volumes of toluene and n-heptane vapor equal to the carbon tetrachloride vapor volume, 10 times the carbon tetrachloride vapor volume, and 100 times the carbon tetrachloride vapor volume were added to Tedlar bags. Between individual Tedlar bag readings, the units were rezeroed using a Tedlar bag blank containing dry air only. A second set of responses was obtained in which the units were rezeroed using a Tedlar bag blank containing the appropriate volume of toluene or n-heptane vapor environment in which the carbon tetrachloride response was being evaluated.

Soil Spiking

The H-10PM and XP-1 units were evaluated for their response to carbon tetrachloride spiked into soil contained inside the Tedlar bags. These experiments were used to compare VOC in soil concentrations (mg VOC/Kg soil) with VOC in air concentrations (vppm).

Sensor Interchangeability

All three units were evaluated for replacement sensor interchangeability. Carbon tetrachloride vapor responses were obtained for five sensors for the H-10PM and the H-10A and for four sensors for the XP-1. Since the sensor response of the H-10PM heated diode sensor can be altered via temperature adjustment, studies were conducted to see if the five individual sensors could be "tuned" to produce similar response profiles.

RESULTS AND DISCUSSION

Sensor Response

Sensor response was evaluated by isolating variables such as VOC type and potential interferences. Responses were evaluated for two distinctly different types of halogenated VOCs; one without double bonds, carbon tetrachloride; and one with a double bond, tetrachloroethylene. The response characteristics were determined for the VOCs directly in headspace, without soil, in containers such as Tedlar bags. Quantitation limits were estimated based on a signal to noise ratio of 10. Potential interferences from volatile hydrocarbons, such as toluene and heptane, were evaluated. The effect of humidity was studied also.

Yokogawa Heated Diode Sensor

Model H-10PM Description

The heated diode sensor was a model H-10PM refrigerant leak detector from Yokogawa Corporation, Newnan, Georgia (Figure 1). The diode is heated between temperatures ranging from about 600–1,000 °C (1,112–1,832 °F). It selectively interacts with halogens present in the volatile organic compounds that it encounters. This is based on positive ion emission technology, wherein halogens cause an ionized current to flow. The device has an on-board sampling pump that operates at two flow rates that control the device's sensitivity. The low flow rate provides the most sensitivity, while the highest flow rate provides the least sensitivity. Sensitivity can also be controlled by adjusting the temperature of the diode heater, with a higher temperature providing greater sensitivity. There is an audio alarm with a chirping sound that is indicative of the amount of volatile halogenated compounds present. Since there is no visual readout, the device was modified according to instructions from the manufacturer by CF Electronics, Laramie, Wyoming, to provide an output signal that ranges from 0 to 15 V. The output was connected to a Linseis L200E strip chart recorder.

The H-10PM has an autozero function that provides steady readings when the unit is in this mode. It also has three sensitivity settings; small, medium, and large. The small setting provides the most sensitivity. The settings alter the amplified signal by changing the air flow rate to the detector, and by electronic attenuation. The small setting uses a pump flow rate of 110 mL/min, while the medium and high settings use a pump flow rate of 160 mL/min.

The H-10PM also has a sensor temperature adjustment that must be used to periodically adjust the sensor response when a reading is made by diffusion from a small vial containing a sample of refrigerant provided by the manufacturer. Over time, the sensor begins to lose its sensitivity. A temperature adjustment restores its response profile to its former state to give responses similar to earlier measurements. Eventually, the diode is spent and it must be replaced with a new one.

Carbon Tetrachloride

Figure 2:
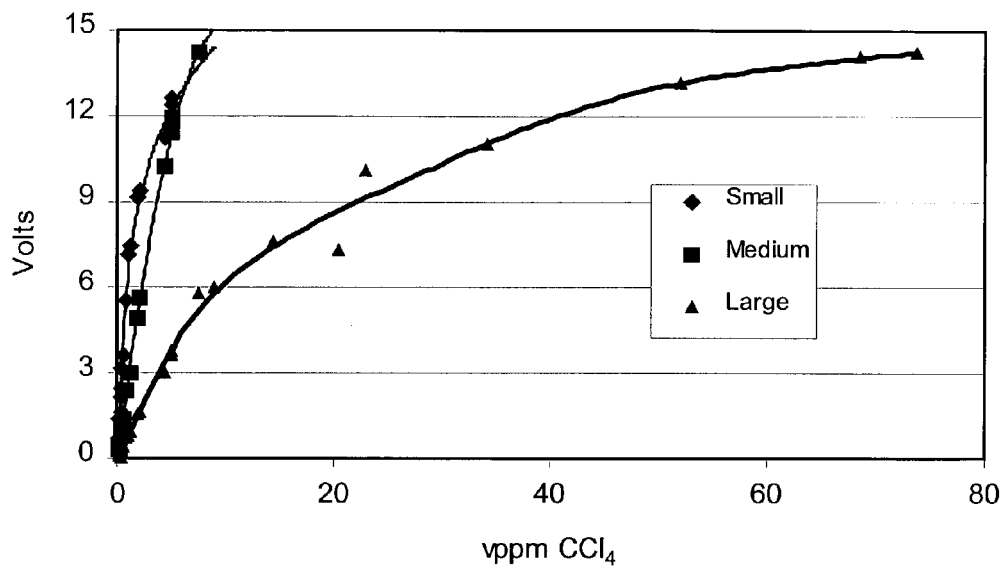
FIG. 2 is a Response Profile of Yokogawa H-10PM
Figure 3:
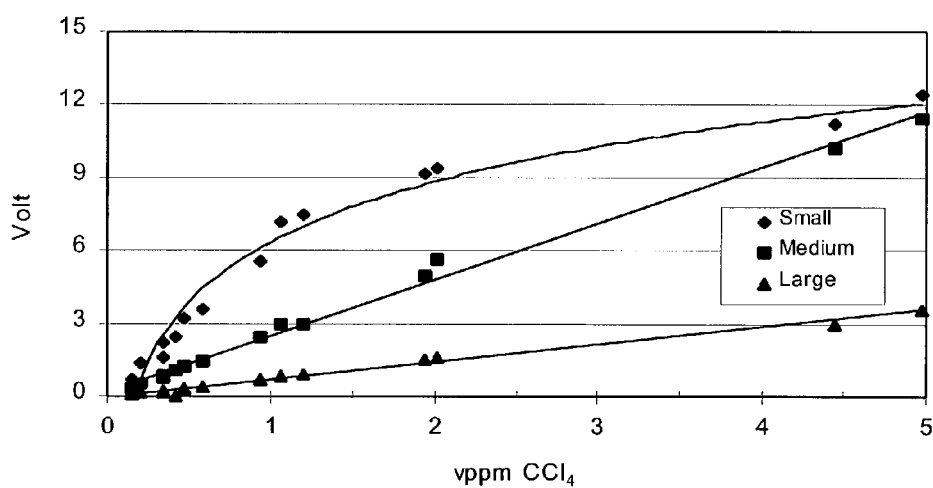

Figure 2 shows the response profile of the H-10PM to carbon tetrachloride vapor in dry air for each of the unit's three settings. The profile for the large setting is the most comprehensive, but also the most non-linear. The unit's response has approached an upper range limit of about 80 vppm where the heated diode response has maximized on the large setting. Figure 3 is an expanded view of the lower working range of the unit, and illustrates the region from near the detection limit up to 5 vppm carbon tetrachloride. A detection limit of 0.2 vppm was calculated with the strip chart recorder using a signal to noise ratio of 10 on the small setting. Note that the linear range of the small setting is rather narrow, from 0.2 to about 1 vppm.

Water Vapor

Figure 4:
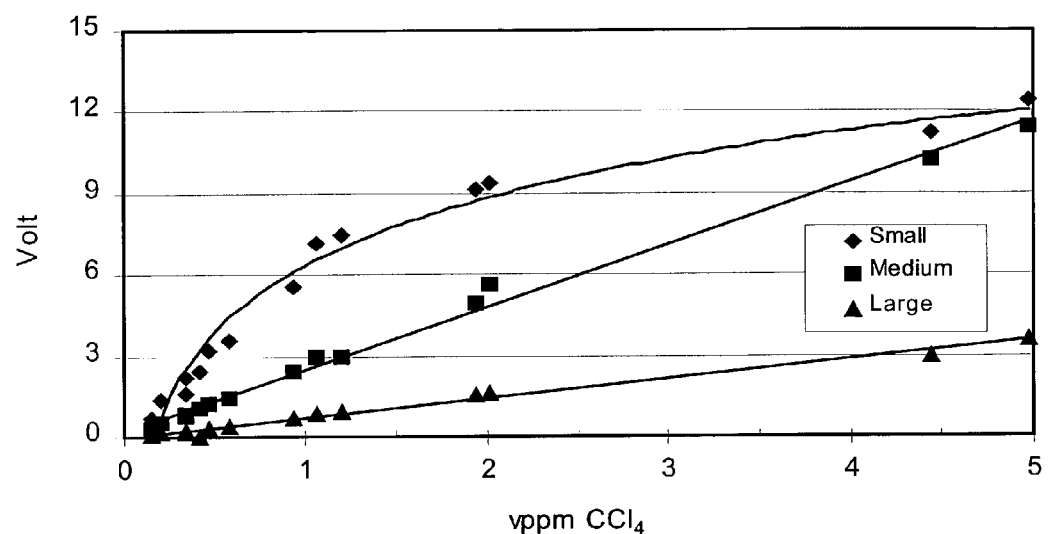
FIG. 4 is a Yokogawa H-10PM Response Profile in Saturated Water Vapor Environment

The H-10PM was evaluated for its response to water vapor. The response of the unit on the small setting to saturated water vapor at 25 °C (77 °F) was found to be equivalent to about 0.095 vppm carbon tetrachloride in dry air. Likewise, the medium setting yielded 0.092 vppm, and the large setting produced a response equivalent to 0.014 vppm. Although the unit does exhibit a slight response to 100% relative humidity, the presence of water vapor can be considered insignificant for two reasons. First, the response profile of carbon tetrachloride vapor in the presence of saturated water vapor (Figure 4) is almost identical to that in dry air (Figure 3). Second, proper use of the unit as an analytical tool would require that it be periodically rezeroed, which could simply be performed in the ambient humid air background. This would serve to effectively cancel out the small contribution of humidity in the response.

Toluene and n-Heptane Response

Figure 5:
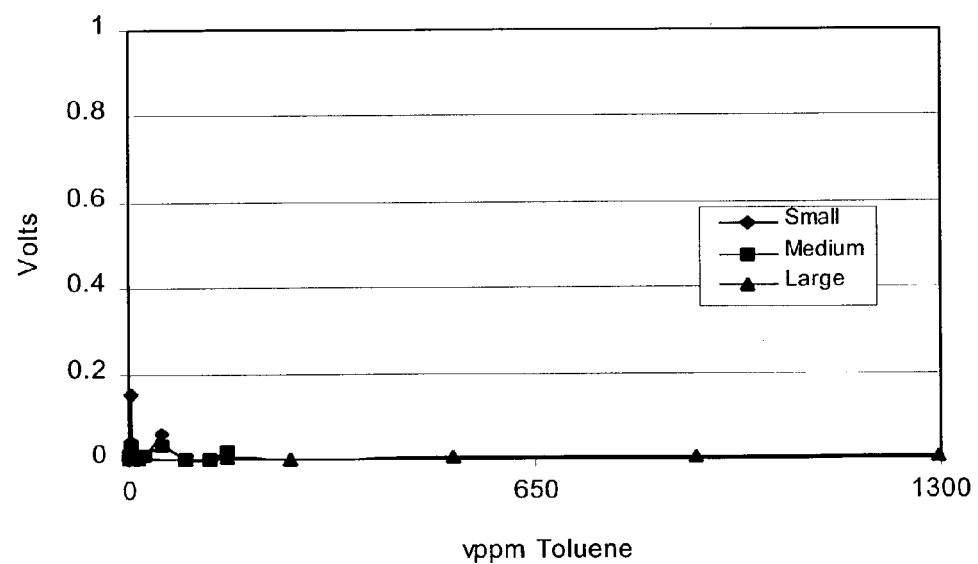
FIG. 5 is a Yokogawa H-10PM Response to Toluene Vapor
Figure 6:
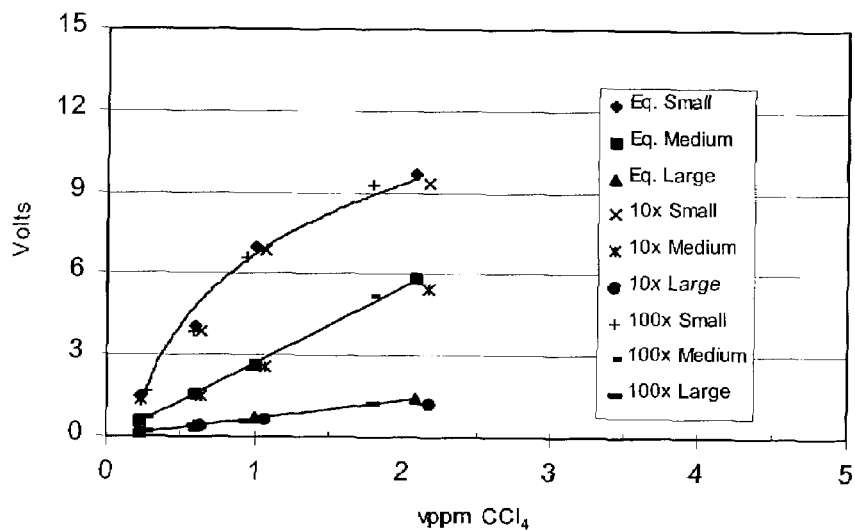
FIG. 6 is a Yokogawa H-10PM Response Profile in Toluene Vapor Environment

The response of the H-10PM to toluene vapor is minimal, as shown as Figure 5. Note that all of the responses for the three settings are below 0.2 volts on the Y axis, compared to a high of 15 volts previously found to define the upper range of the three settings. The large setting, in particular, produces almost no response to toluene vapor. In addition, Figure 6 demonstrates that the presence of toluene vapor does not significantly alter the response profile of the heated diode to carbon tetrachloride vapor (as compared with Figure 3). Actual volumes of toluene used for these experiments were a volume equal to that of carbon tetrachloride, 10 times that of carbon tetrachloride, and 100 times that of carbon tetrachloride. These volumes represent toluene vppm concentrations of 0.25, 2.5, and 25 times that of carbon tetrachloride vppm concentrations, based on relative vapor pressures at ambient temperature.

Figure 7:
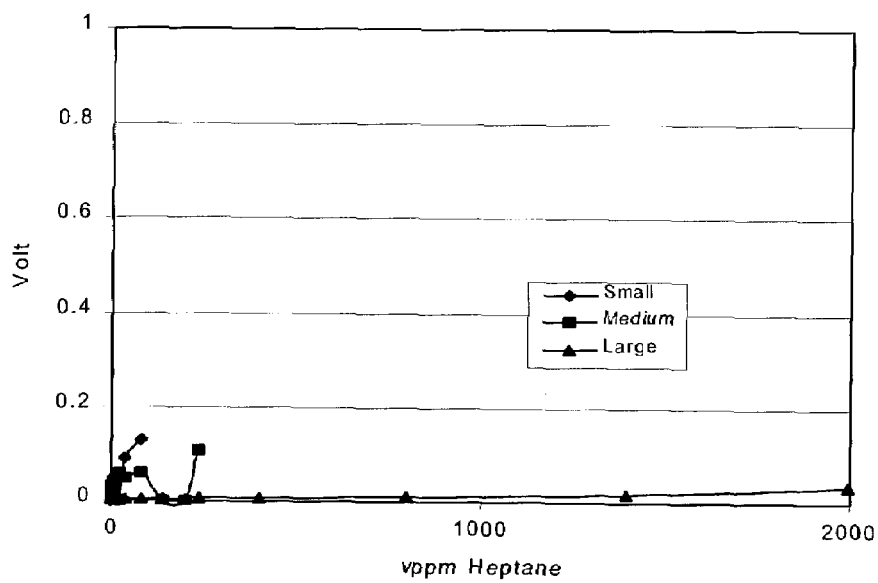
FIG. 7 shows a Yokogawa H-10PM Response to n-Heptane Vapor.
Figure 8:
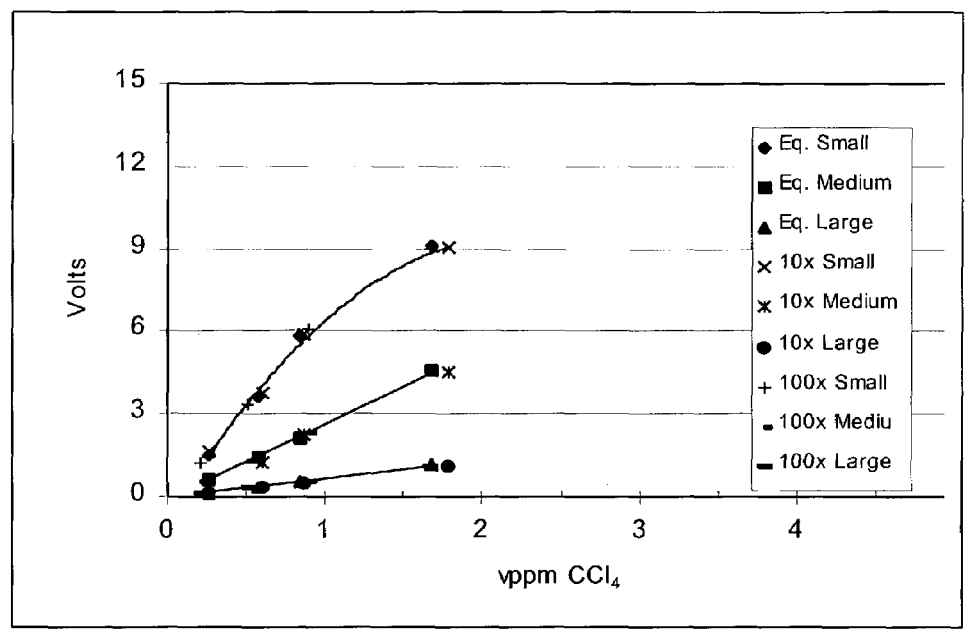
FIG. 8 is a Yokogawa H-10PM Response in n-Heptane Vapor Environment

The response of the H-10PM to n-heptane vapor is also minimal, as shown in Figure 7. As with toluene, all three settings produce responses less than 0.2 volts, and the large setting produces essentially no response. Figure 8 demonstrates that the presence of n-heptane vapor does not significantly alter the response profile of the heated diode to carbon tetrachloride vapor, and is almost identical to Figure 3. Actual volumes of n-heptane used were a volume equal to that of carbon tetrachloride, 10 times that of carbon tetrachloride, and 100 times that of carbon tetrachloride. These volumes represent n-heptane vppm concentrations of 0.4, 4.0, and 40 times that of carbon tetrachloride vppm concentrations, based on relative vapor pressures at ambient temperature.

Sensor Interchangeability and Tuning

Figure 9:
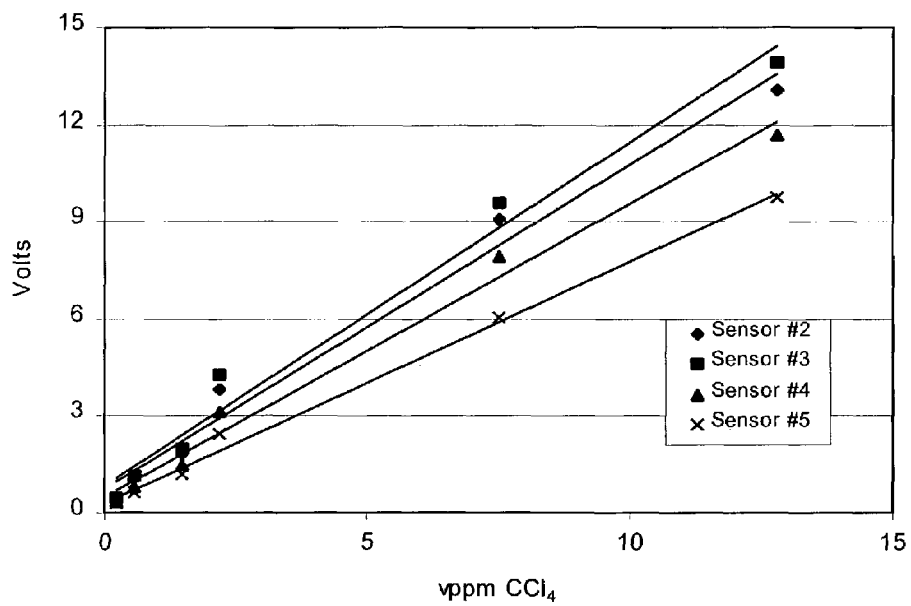
FIG. 9 is a Yokogawa H-10PM Sensor Interchangeability
Figure 10:
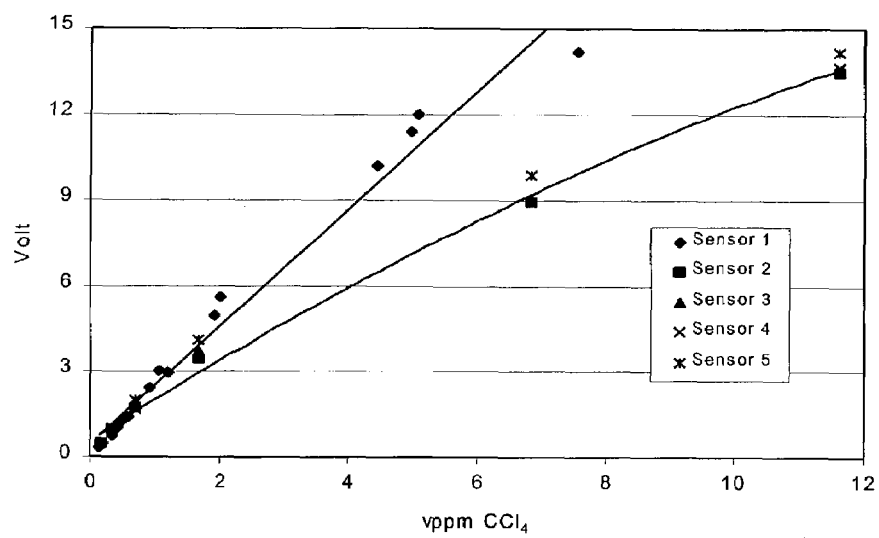
FIG. 10 is a Yokogawa H-10PM Sensor Comparison with Temperature Adjustment

At this point in the study, it was observed that the original sensor diode (sensor #1) was starting to give inconsistent results when compared to previous data. The temperature of the sensor was changed in several attempts to restore it to original performance. This proved unattainable, suggesting that the sensor was spent and therefore, required replacement. Four replacement sensor diodes (#2 through #5) were subsequently evaluated using carbon tetrachloride vapor. Figure 9 shows the variability between sensors #2 through #5 at identical temperature settings. Based on these data, experiments were then conducted to "tune" the sensors to give similar response profiles. Raising the temperature of the sensors made them more sensitive (and vice versa), and Figure 10 shows that sensors #2 through #5 could indeed be tuned to yield similar response profiles. However, at higher vppm concentrations, the tuned response profiles of the replacement sensors were found to be significantly different from the response profile of original sensor #1. It is unclear whether this is indicative of an electronic problem related to long-term unit operation, or simply random variation between experiments conducted months apart.

Soil Spiking

Figure 11:
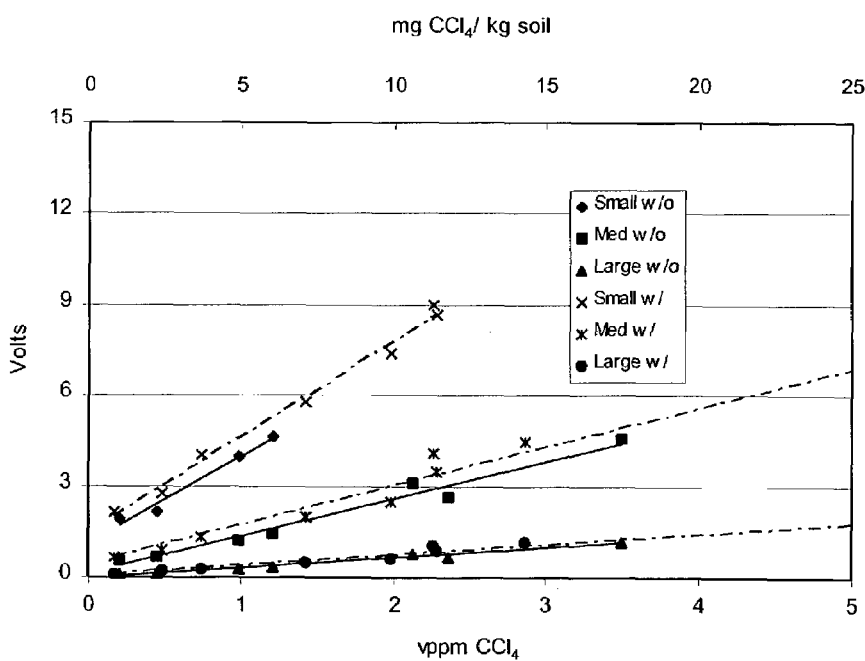
FIG. 11 is a Yokogawa H-10PM Soil Spiking Results

Sensor #2 was employed for the soil spiking study, using a riverbank soil obtained locally. One-gram portions of soil were weighed into individual Tedlar bags, and various concentrations of carbon tetrachloride in a 100-uL methanol aliquot were added to the soil by micropipette. The bags were immediately sealed, and the contents were shaken and allowed to equilibrate overnight. For comparison purposes, aliquots were also spiked into empty Tedlar bags containing no soil. The results of the spiking studies are shown in Figure 11. The slight variation between the empty bag (w/o) and soil spike (w) results is probably due to experimental error, because a subsequent study yielded similar results, but with opposite effect in which the soil spikes produced less response than the empty bag. Of particular interest is the relationship between the spiked mg VOC/Kg soil concentrations and vppm results. This correlation is influenced by the volume of the Tedlar bag (~ 1-L volume), and implies that a lower detection limit and quantitation range can be achieved by decreasing the headspace volume. A hypothetical field method using 2.5 g of soil and 50-mL headspace volume suggests that a 50-fold increase in the detection limit and quantitation range for soil relative to air can be achieved.

Tetrachloroethylene

Relative sensitivities of the heated diode system were measured with a single diode at low, medium, and high sensitivity settings at low, medium, and high concentrations of both carbon tetrachloride and tetrachloroethylene (PCE). The data are presented in Table 2. The response to PCE on the high sensitivity setting was only about 0.42 V, which appears to be near a threshold value for the device. The results for the medium and high sensitivity settings show that the response to tetrachloroethylene is on average only 23% of the response to carbon tetrachloride. Both of these VOCs contain four chlorine atoms. PCE has a double bond. Apparently, the differences between these compounds causes a different reaction with the heated diode that results in different sensitivities.

Table 2. Yokogawa H-10PM Relative Response of Carbon Tetrachloride and Tetrachloroethylene

| Sensitivity | Instrument Setting | Concentration $CCl_4$, vppm | Response V/vppm | Concentration PCE, vppm | Response V/vppm | Response $PCE/CCl_4$ |
|---|---|---|---|---|---|---|
| High | Small | 3.50 | 2.4 | 2.04 | 0.21 | 0.09 |
| Medium | Medium | 14.4 | 0.90 | 11.2 | 0.19 | 0.21 |
| Low | Large | 32.5 | 0.24 | 29.8 | 0.06 | 0.25 |

Average (medium and low): 0.23

TIF Corona Discharge Sensors

Model XP-1 Description

Figure 12:
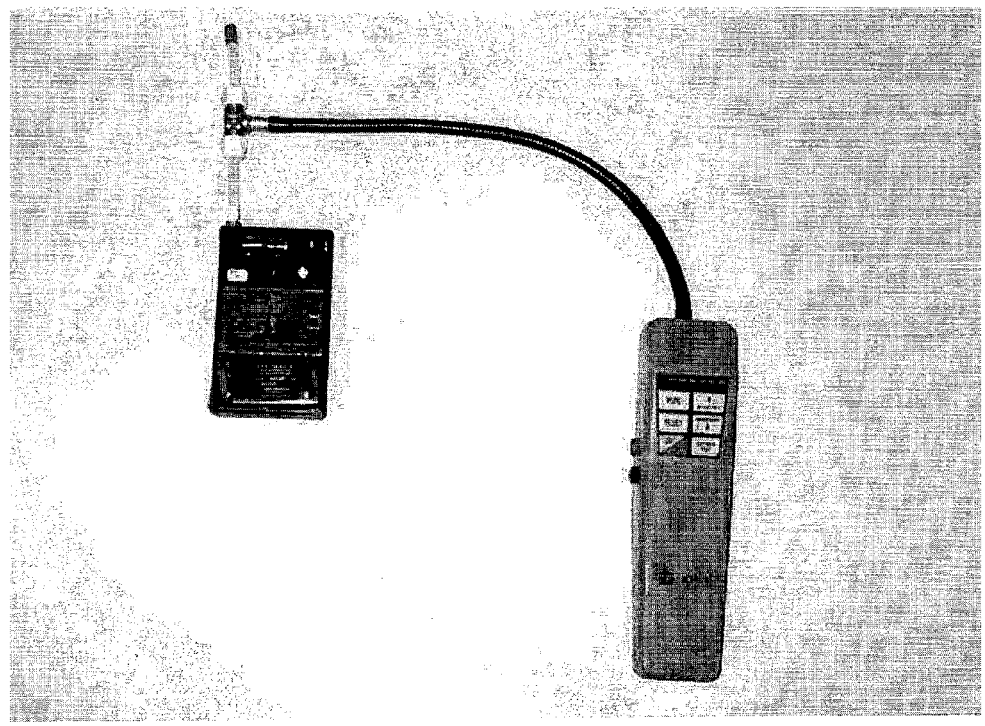
FIG. 12 is a TIF XP-1 Leak Detector with Auxiliary Du Pont P200A Personal Sampling Pump

The corona discharge device with which the initial experimental work was performed was a TIF model XP-1 refrigerant leak detector from ATP, Inc., Miami, Florida (Figure 12). The sensor tip operates at a potential difference of 1,500 to 2,000 VDC. A discharge current of about 10 microamperes is decreased by the presence of halogen-containing VOCs. This perturbation of current is difficult to interpret directly, and the manufacturer has developed a digital signal processing algorithm to convert the change in current and voltage into an audible alarm and a visual readout consisting of a series of lighted diodes on the front panel that relate to the concentration of contaminant. The TIF XP-1 contains a small fan located within the body of the unit that is designed to pull sampled air past the probe tip and through a flexible wand. However, no air flow could be detected at the sensor tip. Subsequent disassembly showed that the fan, either by design or ineffective sealing, was not capable of pulling sampled air through the wand and past the sensor tip. To circumvent this problem, the unit was modified to deliver a constant flow of sampled air past the sensor tip. The pump chosen for this purpose is an air sampling pump usually employed for precise chemical vapor air monitoring in personal hygiene applications. The pump was configured to pull sampled air past the sensor tip upstream from the pump. The sensor tip was fitted into a low-void volume 316 stainless steel "T" carefully machined to eliminate leakage and void volumes, and to provide consistent air flow past the sensor tip. Different pump air flows were initially explored, and a flow rate of 150 mL/min was chosen.

The XP-1 produces an audible beep and an LED readout when chemical vapors are detected. The frequency of the beep, and the color and number of LED lights is proportional to the amount of chemical vapor detected. At the request of WRI, the model XP-1 was custom configured by the manufacturer with two wire leads to the corona discharge detector. The signals produced by these leads were found to be inconsistent. In some instances the wire leads were found to adversely affect the detector by creating artificial signals. The audible beep cannot be used to quantitate or estimate amounts or concentrations of chemical vapors. However, the LED readout can be employed in a somewhat simple fashion to gauge the approximate concentration of chemical vapors. The LED readout of three colors and six lights produces a net signal range of 0 through 18 lights for each of the unit's seven sensitivity levels. The levels electronically attenuate the signal from the corona discharge detector; level 7 is the most sensitive while level 1 is the least sensitive. Sensitivity level 7 and to a lesser degree, 6, could not be used reliably in this study because they were found to give irreproducible and inconsistent results. Reliable signals in laboratory experimentation were generated for levels 1 through 5. For the study, the number of lights was determined by visual means. To reliably employ this device as a quantitative analyzer, a more precise electronic readout would have to be developed.

Carbon Tetrachloride

Figure 13:
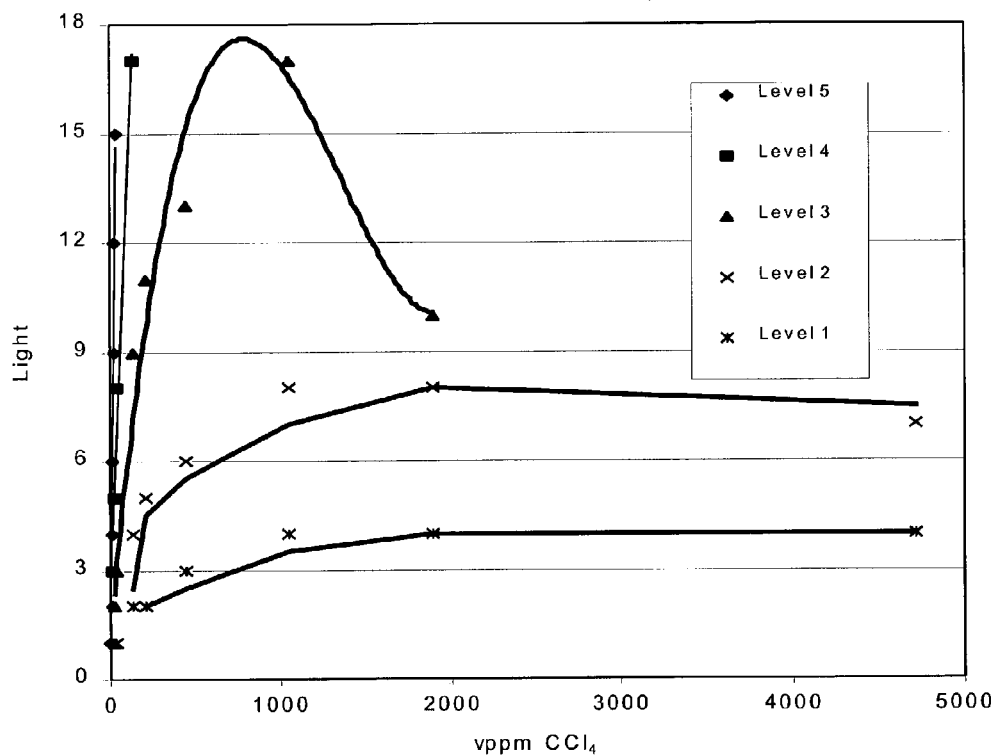
FIG. 13 is a Response Profile of TIF XP-1
Figure 14:
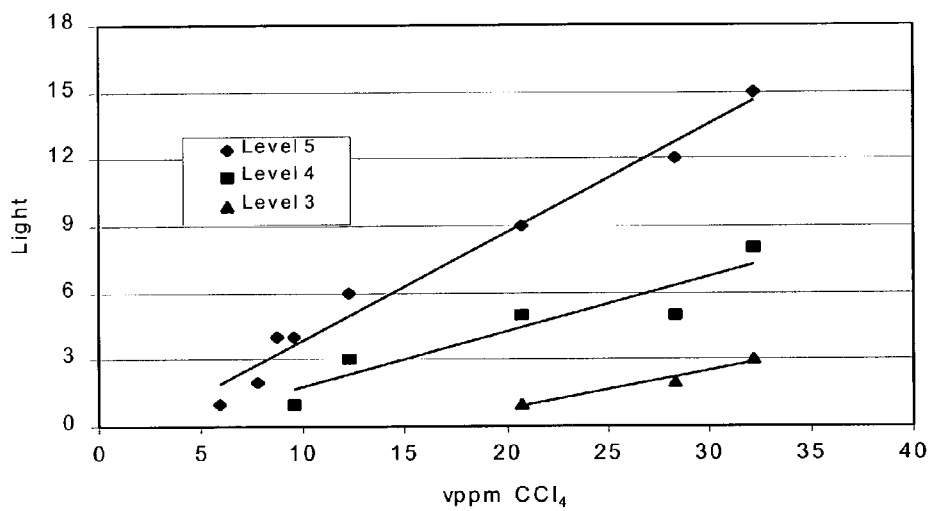
FIG. 14 is a Expanded View of Lower Working Range of TIF XP-1

Figure 13 shows the response profile of the XP-1 to carbon tetrachloride vapor in dry air for each of the unit's five sensitivity levels tested. Maximum responses are reached for levels 3, 4, and 5 at about 1,000 vppm, where it appears that the sensor has become saturated. Figure 14 is an expanded view of the lower working range of the XP-1, and illustrates the region near the detection limit up to about 40 vppm carbon tetrachloride. Using the level 5 setting, a detection limit of approximately 10 vppm can be obtained using the least number of lights that yield a reliable result, which is estimated to be either two or three lights.

Water Vapor

Figure 15:
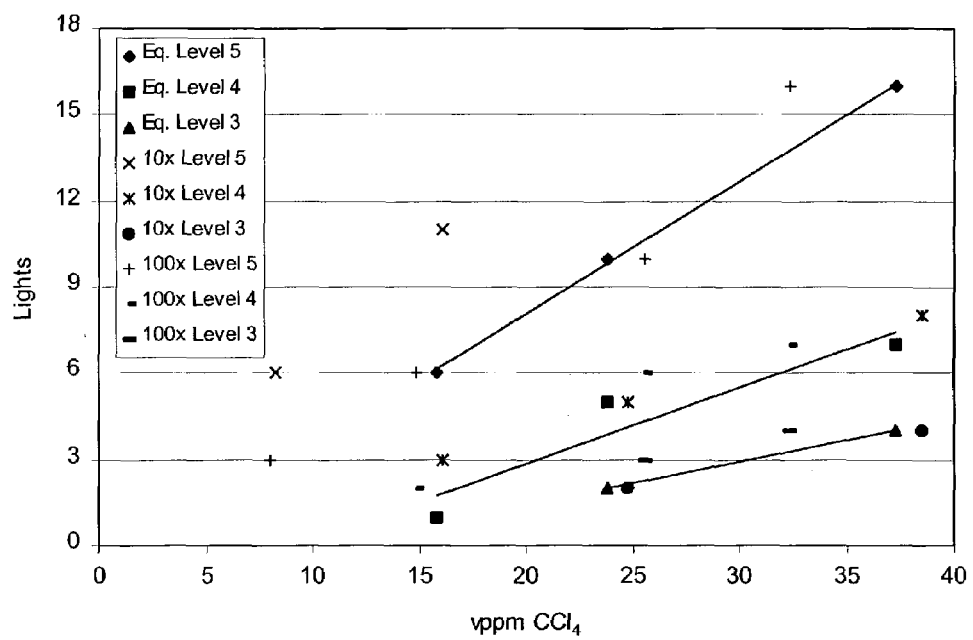
FIG. 15 is a TIF XP-1 Response in Saturated Water Vapor Environment

The TIF XP-1 gives a somewhat pronounced chemical response to saturated water vapor in air at ambient temperature, which is equivalent to approximately 20 vppm of carbon tetrachloride using the level 4 and 5 settings. Thus, the response curve of carbon tetrachloride vapor in combination with 100% relative humidity is the combined sum of the two individual responses. However, as shown in Figure 15, if the XP-1 is rezeroed in the 100% relative humidity environment, the response curve of carbon tetrachloride vapor in combination with saturated water vapor is within experimental error to that of carbon tetrachloride in dry air (Figure 14). Thus, proper use of the unit as an analytical tool would require that it be periodically rezeroed in the proper ambient humidity air background.

Toluene and n-Heptane

Figure 16:
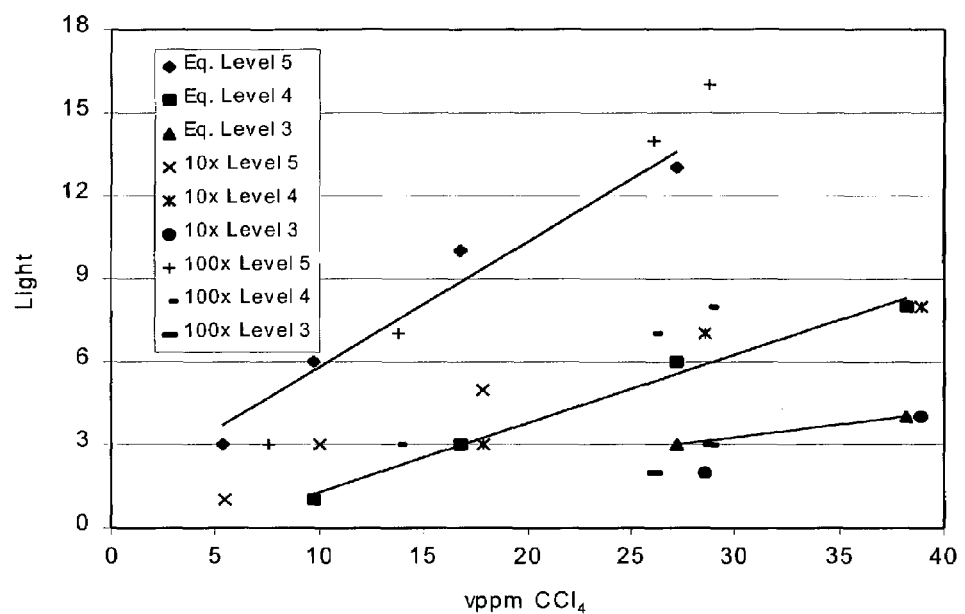
FIG. 16 is a TIF XP-1 Response in Toluene Vapor Environment
Figure 17:
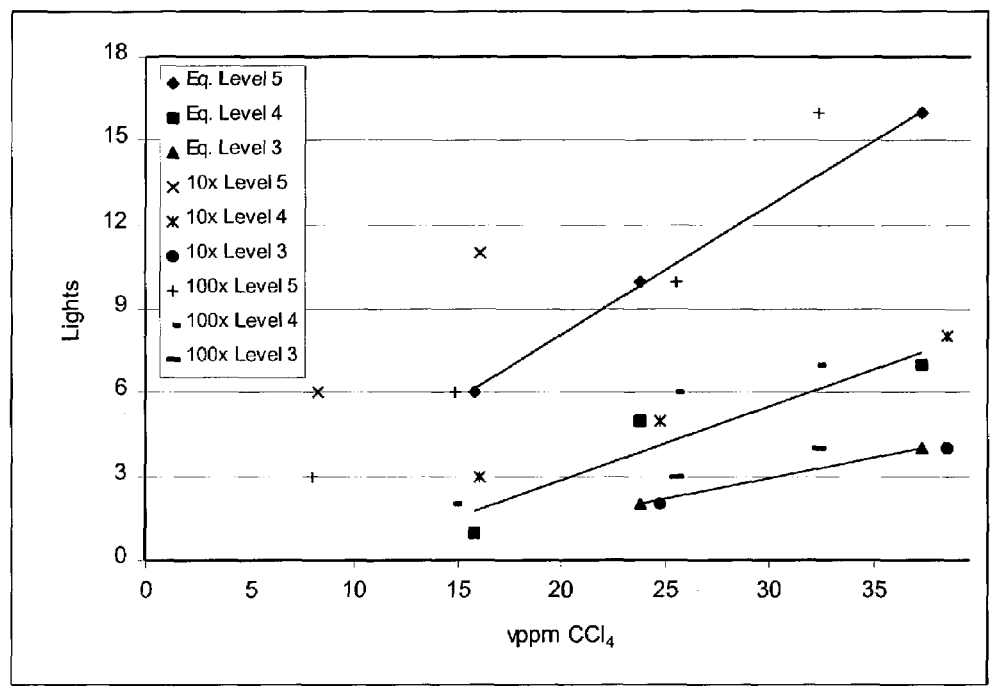
FIG. 17 is a TIF XP-1 Response Profile in n-Heptane Vapor Environment

Toluene vapor at concentrations as high as 1,300 vppm did not give a response on the XP-1. Figure 16 demonstrates that the presence of toluene vapor does not significantly alter the response profile of the corona discharge to carbon tetrachloride vapor. Figure 16 is roughly equivalent to Figure 14. Actual volumes of toluene used for these experiments were a volume equal to that of carbon tetrachloride, 10 times that of carbon tetrachloride, and 100 times that of carbon tetrachloride. These volumes represent toluene vppm concentrations of 0.25, 2.5, and 25 times that of carbon tetrachloride vppm concentrations, based on relative vapor pressures at ambient temperature. Figure 16 does show a rather pronounced error in response, as reflected in the poor precision of some of the data points. This observed lack of precision could be due to detector noise, the ambiguity of reading the LED lights, or perhaps even due to poor air flow characteristics past the sensor tip in the "T."

n-Heptane vapor at concentrations as high as 2,000 vppm did not give a response on the XP-1. Figure 17 demonstrates that the presence of n-heptane vapor does not significantly alter the response profile of the corona discharge to carbon tetrachloride vapor; Figure 17 is roughly equivalent to Figure 14. Actual volumes of n-heptane used for these experiments were a volume equal to that of carbon tetrachloride, 10 times that of carbon tetrachloride, and 100 times that of carbon tetrachloride. These volumes represent n-heptane vppm concentrations of 0.4, 4.0, and 40 times that of carbon tetrachloride vppm concentrations, based on relative vapor pressures at ambient temperature. As previously observed in the toluene environment studies, there was a relatively poor precision in the carbon tetrachloride response in the n-heptane vapor environment.

Soil Spiking

Figure 18:
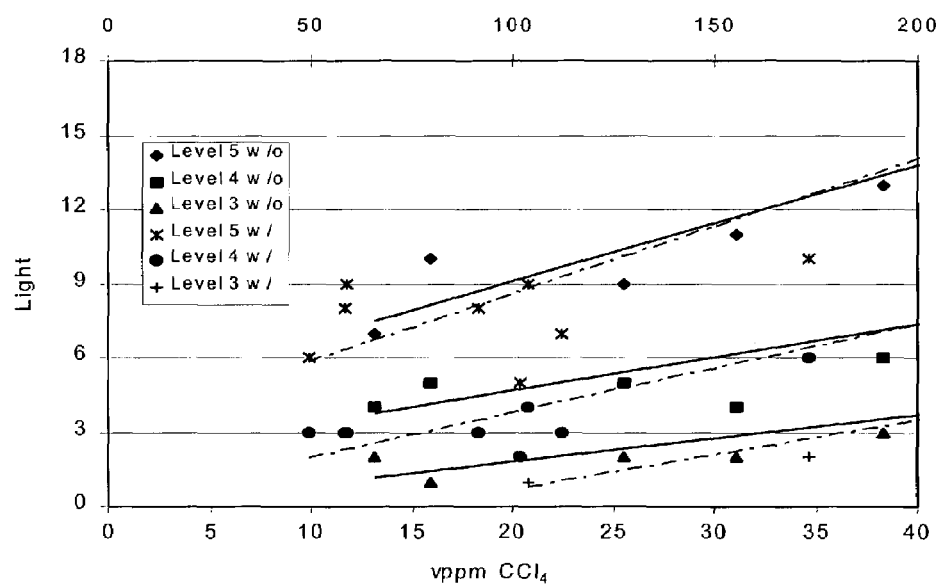
FIG. 18 shows TIF XP-1 Soil Spiking Results.

The soil spiking study was conducted using a riverbank soil obtained locally. One-gram portions of soil were weighed into individual Tedlar bags, and various concentrations of carbon tetrachloride in a 100-uL methanol aliquot were added to the soil by micropipette. The bags were immediately sealed, and the contents were shaken and allowed to equilibrate overnight. For comparison purposes, 100-uL aliquots were also spiked into empty Tedlar bags containing no soil. The results of the spiking studies are shown in Figure 18. Any variation between the soil spike data (w) and the empty bag data (w/o) is unobservable due to the lack of precision in the data, as noted above. Of particular interest is the relationship between the spiked mg VOC/Kg soil concentrations and vppm results. This correlation is influenced by the volume of the Tedlar bag (~ 1-L volume), and implies that a lower detection limit and quantitation range can be achieved by decreasing the headspace volume or increasing the amount of soil.

Sensor Interchangeability

Figure 19:
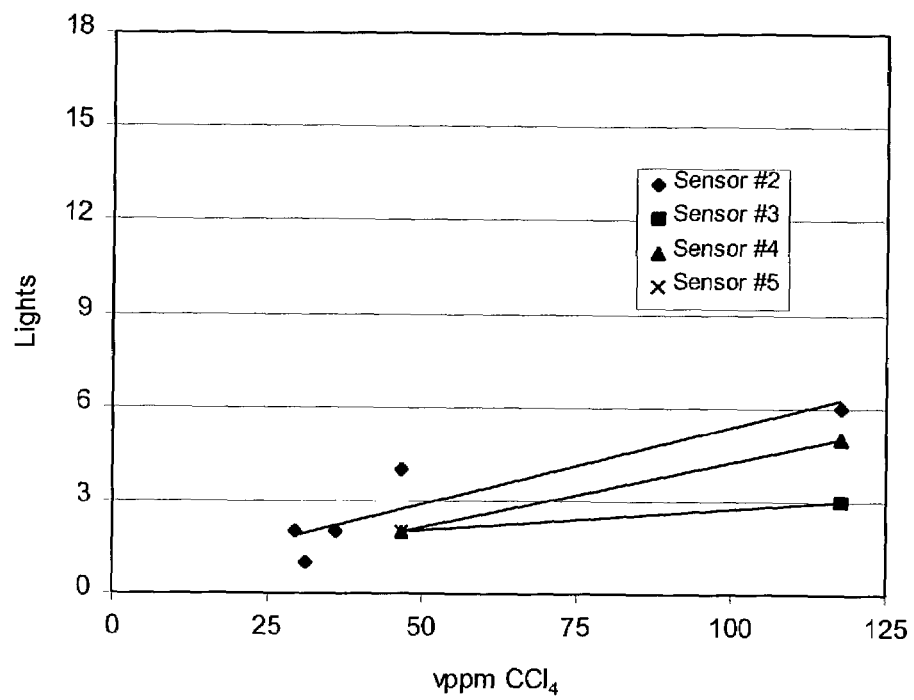
FIG. 19 is a TIF XP-1 Sensitivity Level 3, Sensor Interchangeability
Figure 20:
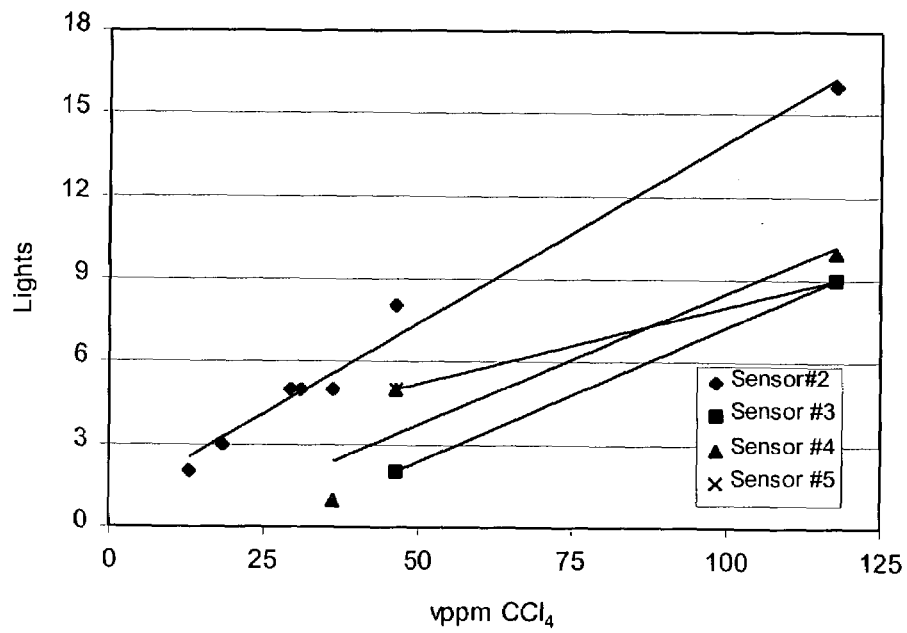
FIG. 20 is a TIF XP-1 Sensitivity Level 4, Sensor Interchangeability
Figure 21:
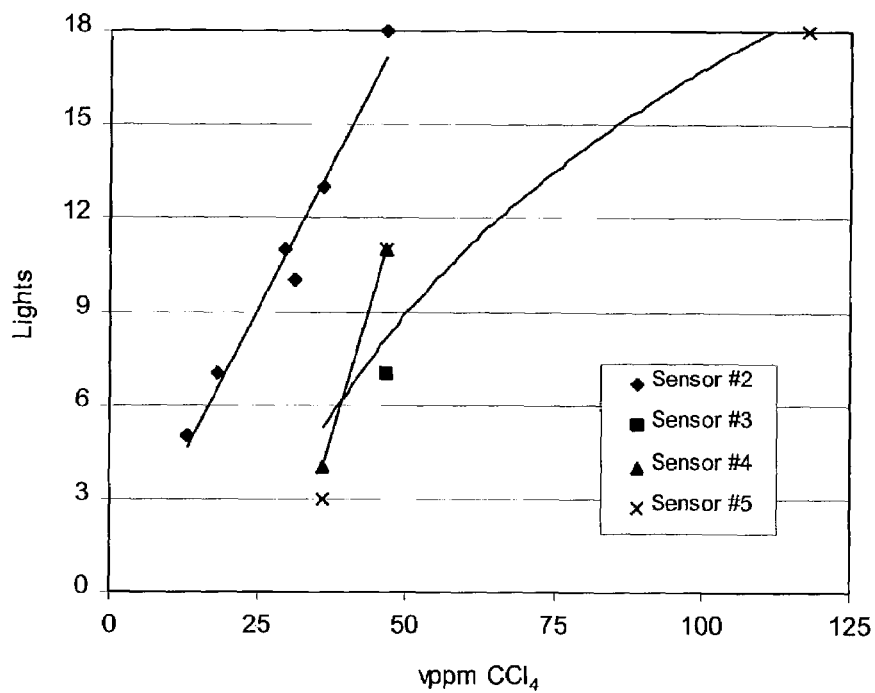
FIG. 21 is a TIF XP-1 Sensitivity Level 5, Sensor Interchangeability

The studies described above were conducted using one of the two original sensor tips shipped with the unit, which was labeled sensor #2 in the laboratory. Three replacement sensors (#3 through #5) were subsequently evaluated for their response to carbon tetrachloride vapor. Figure 19 shows the relative responses of the different sensors at sensitivity level 3; Figure 20 shows them at sensitivity level 4; and Figure 21 shows them at sensitivity level 5. There is a wide variation in response between the individual sensors, which is especially evident at the more sensitive level 5 setting. These variations would have to be overcome, either by quality control or by individual sensor calibration, for the XP-1 to be used as a quantitative tool.

Model H-10A Description

Figure 22:
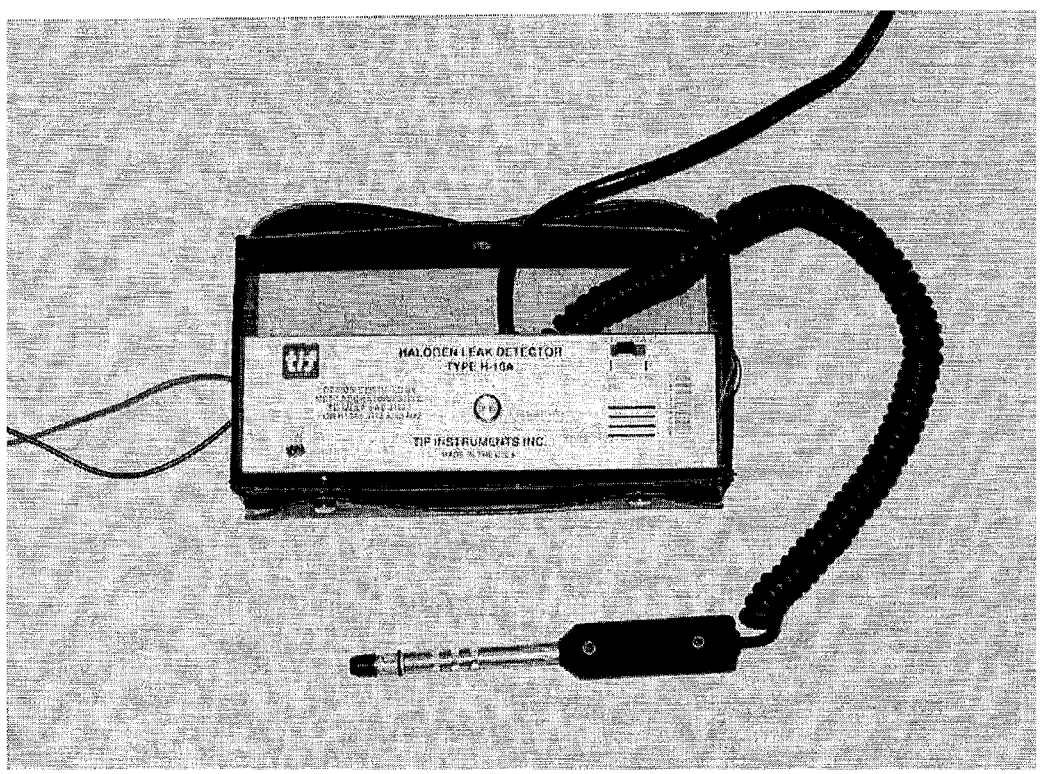
FIG. 22 is a TIF H-10A Leak Detector

The TIF H-10A (Figure 22) is a corona discharge refrigerant leak detector unit with some different design features from the XP-1. It operates on 115 V and contains a small fan located in close proximity to the sensor tip, which proved to be a better design for air flow purposes than the design of the TIF XP-1. Reliable readings were obtained by inserting the probe tip directly into the Tedlar bags, without having to use the "T" fitting and sampling pump that were required for the TIF XP-1.

The H-10A uses a flashing neon light and an audible popping signal that increases in frequency as higher amounts of halogen are detected. Since the audible frequency cannot be used directly to estimate amounts or concentrations of chemical vapors, the unit was modified by CF Electronics, Laramie, Wyoming, to provide wire leads interfaced from the audible output to a multimeter that provided a readout of the frequency in Hz. In this fashion, a reliable quantitative frequency reading from about 1–300 Hz could be recorded.

The H-10A was obtained at WRI rather late in the initial study, after the humidity, toluene, n-heptane, and soil spiking experiments had all been performed for the TIF XP-1. However, the purpose in evaluating the H-10A was not so much for its corona discharge response profiles, because these had already been suitably obtained for the TIF XP-1. Rather, the main purpose in evaluating the H-10A was for its overall design features that distinguished it from the XP-1.

Carbon Tetrachloride

Figure 23:
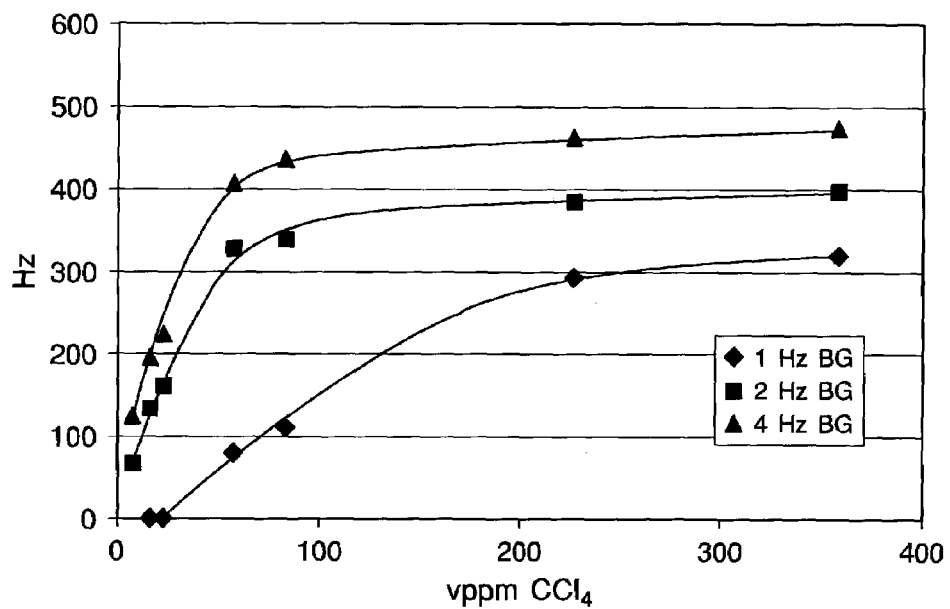
FIG. 23 is a Response Profile of TIF H-10A

Figure 23 shows the response profile for carbon tetrachloride vapor in dry air for a single sensor tip using a background blank setting of 1, 2, and 4 Hz. The 1-Hz background setting is the least sensitive, and the 4-Hz setting is the most sensitive. Higher background settings provide erratic results. As shown in Figure 23, the lower working range of the H-10A is fairly equivalent to that of the XP-1, in the vicinity of 10 to 25 vppm carbon tetrachloride. The quantitation limit is about 10 vppm. The ability of the operator to read a frequency signal from a digital meter makes this design more attractive for quantitative work than reading the number of lights in the XP-1 display. Therefore, this unit was used for subsequent experiments.

Sensor Interchangeability

Figure 24:
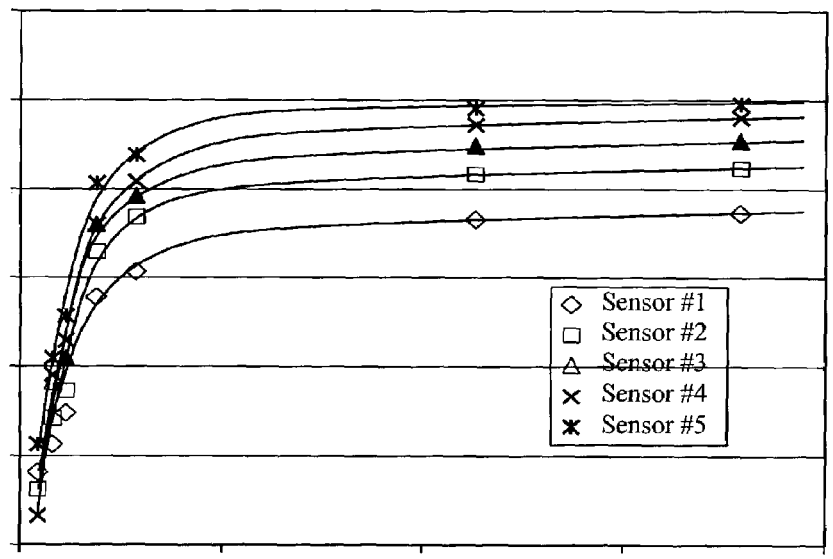
FIG. 24 is TIF H-10A Sensor Interchangeability

The studies described above were conducted using the two original sensor tips shipped with the unit. Three replacement sensors (#3 through #5) were subsequently evaluated for their response to carbon tetrachloride vapor. Figure 24 shows the relative responses of the different sensors at the medium blank sensitivity setting of 2 Hz. There is some variation evident in response between the individual sensors.

Tetrachloroethylene

Relative sensitivities of the corona discharge system were measured with a single sensor tip for low, medium, and high sensitivity settings for low, medium, and high concentrations of both carbon tetrachloride and tetrachloroethylene (PCE). The data are presented in Table 3. The results show that the response to tetrachloroethylene is essentially identical to the response to carbon tetrachloride. Both of these VOCs contain four chlorine atoms. PCE has a double bond. Apparently, the presence of the double bond does not affect the response or the ability of the chlorine atoms to capture electrons in the corona.

Table 3. TIF H-10A Relative Response of Carbon Tetrachloride and Tetrachloroethylene

| Sensitivity | Instrument Setting | Concentration $CCl_4$, vppm | Response Hz/vppm | Concentration PCE, vppm | Response Hz/vppm | Response $PCE/CCl_4$ |
|---|---|---|---|---|---|---|
| High | 4 Hz | 30.8 | 7.38 | 29.2 | 7.15 | 0.97 |
| Medium | 2 Hz | 91.0 | 3.43 | 87.7 | 4.15 | 1.21 |
| Low | 1 Hz | 297 | 1.06 | 297 | 0.94 | 0.89 |
| | | | | | Average: | 1.02 |

Elements of a New Analytical Method

As discussed above, the performance of the new devices was evaluated in the laboratory by spiking soil samples and monitoring headspace for halogenated VOCs. A draft concept of the steps required to develop new analytical methods with these devices would require a number of considerations. These include sample collection, the container from which headspace would be sampled, and the interpretation of the signal from the sensor system. Since samples would be contaminated with VOCs, consideration must be made for collecting the sample with as little handling and loss as possible. Prior to headspace screening analysis, the sample should be placed in a container that has the ability to contract as the headspace is being drawn out, to prevent dilution by outside air. This would possibly involve using 5 g of a 25-g soil sample and 250-mL to 500-mL headspace volume. Calibration of the sensor device would be with a controlled leak source such as those available from sensor manufacturers, or standardization from a known amount of a particular VOC such as carbon tetrachloride in a Tedlar bag. Possibly, the soil sample could be dried with a drying agent prior to analysis; however, the heat generated could cause the VOC contaminants to rapidly enter the headspace. Water should not be added to the soil sample. Prior results in our laboratory show that this adds an additional complexity in that complex VOC equilibria between soil and water and air would apply, and headspace results are generally lower than when evaluating the sample directly. Quantitation limits and dynamic analytical ranges could be altered by changing the soil to air ratios and possibly temperature.

CONCLUSIONS

Commercially available heated diode and corona discharge leak detectors were obtained from the manufacturers. These were modified to provide readouts that correspond to the concentration of halogenated VOCs in air. Sensor response was evaluated with carbon tetrachloride and tetrachloroethylene (perchloroethylene, PCE), which represent halogenated VOCs with and without double bonds. The response characteristics were determined for the VOCs directly in headspace, without soil, in containers such as Tedlar bags. Quantitation limits were established at a S/N ratio of 10. Potential interferences from volatile hydrocarbons, such as toluene and heptane, were evaluated and found to be nonexistent. The effect of humidity was studied also. Humidity did not change the response profiles, and small responses due to humidity could be zeroed out. Soil spiking experiments were conducted also. These showed that the VOCs measured in the headspace with the modified leak detectors could be used to screen halogenated VOC concentrations in soil. A draft concept of the steps required to develop new analytical methods with these devices was prepared.

REFERENCES

Adams, J.W., W.M. Davis, E.R. Cespedes, W.J. Buttner, ans M.W. Findlay, 1997, Development of Cone Penetrometer Electrochemical Sensor Probes for Chlorinated Solvents and Explosives, Field Analytical Methods for Hazardous Wastes and Toxic Chemicals, Conference Proceedings, Air & Waste Management Association, Pittsburgh, PA, 667-670.

American Society for Testing and Materials, 2000, D-5831-96, Standard Test Method for Screening Fuels in Soils. *Annual Book of ASTM Standards*, Vol. 11.04, 319-326.

Buttner, W.J., W.R. Penrose, J.R. Stetter, C.E. Christy, and C. Naklaishi, 1995, A Hand-Portable Instrument System for Real-Time Analysis of Chlorinated Organic Compound Contamination, Field Screening Methods for Hazardous Wastes and Toxic Chemicals, Conference Proceedings, Volume 2, Air & Waste Management Association, Pittsburgh, PA, 702-712.

Driscoll, J.N. and J.H. Becker, 1979, Industrial Hygiene Monitoring with a Variable Selectivity Photoionization Detector, American Laboratory, 11 (11): 101-110.

Ewing, K.J., T. Bilodeau, G. Nau, F. Bucholtz, and I.D. Aggarwal, 1995, Fiber Optic Raman Volatile Organic Compound Sensor, Field Screening Methods for Hazardous Wastes and Toxic Chemicals, Vol. 1, Conference Proceedings, Air & Waste Management Association, Pittsburgh, PA, 364-371.

Frye, G.C., D.W. Gilbert, C. Colburn, R.W. Cernosek, and T.D. Steinfort, 1995, Above-Ground In-Situ Field Screening of VOCs Using a Portable Acoustic Wave Sensor (PAWS), Field Screening Methods for Hazardous Wastes and Toxic Chemicals, Volume 2, Conference Proceedings, Air & Waste Management Association, Pittsburgh, PA, 715-726.

Haas, J.W., M.M. Carraba, and R.W. Forney, 1995, Nonaqueous Phase Liquids: Searching for the Needle in the Haystack, Field Screening Methods for Hazardous Wastes and Toxic Chemicals, Vol. 1, Conference Proceedings, Air & Waste Management Association, Pittsburgh, PA, 443-449.

Hewitt, A.D. and N.J. Lukash, 1997, Rapid Method for Estimating the Total Concentration of Volatile Organic Compounds in Soil Samples, Field Analytical Methods for Hazardous Wastes and Toxic Chemicals, Conference Proceedings, Air & Waste Management Association, Pittsburgh, PA.

REFERENCES (continued)

Hudak, R., J. Melby, D. Onisk, and J. Stave, 1995, Validation of an Immunoassay Field Screen for Trichloroethylene (TCE), Field Screening Methods for Hazardous Wastes and Toxic Chemicals, Vol. 1, Conference Proceedings, Air & Waste Management Association, Pittsburgh, PA 101-108.

Kerndorff, H., R.H. Plumb, R. Schleyer, and G. Milde, 1992, Anthropogeochemistry of Ground-Water Pollutants from Waste Sites, in Lesage, S. and R.E. Jackson, eds., Groundwater Contamination and Analysis at Hazardous Waste Sites. Marcel Dekker, New York, NY, 245-271.

Le Goullon, D. and K. Goswami, 1990, Fiber Optic Refractive Index Sensor Using a Metal Clad. U.S. Patent 4,929,049.

Linenberg, A., 1995, On-Site Monitoring of Vinyl Chloride at Part Per Trillion Levels in Air, Field Screening Methods for Hazardous Wastes and Toxic Chemicals, Vol. 1, Conference Proceedings, Air & Waste Management Association, Pittsburgh, PA, 236- 245.

Milanovich, F.P., S.B. Brown, B.W. Colstron, Jr., P.F. Daley, and K.C. Langry, 1994, A Fiber-Optic Sensor System for Monitoring Chlorinated Hydrocarbon Pollutants, Talanta, 41 (12), 2189-2194.

Milanovich, F.P., D.G. Garvis, S.M. Angel, S.M. Klainer, and L. Eccles, 1986, Remote Detection of Organochlorides with a Fiber Optic Sensor. Analytical Instrumentation, 15, 137-147.

Myers, K.F., J.M. Brannon, R.A. Karn, C.B. Price, D.Y. Eng, A.B. Strong, and S.S. Cooper, 1995, Laboratory Evaluation of a Volatile Organic Compound Analysis System for the Site Characterization and Analysis Demonstration System, Field Screening Methods for Hazardous Wastes and Toxic Chemicals, Vol. 1, Conference Proceedings, Air & Waste Management Association, Pittsburgh, PA, 177-184.

Olsen, K.B., J.W. Griffin, D.A. Nelson, B.S. Matson, and P.A. Esbach, 1989, Prototype Design and Testing of Two Fiber Optic Spectrochemical Emission Sensors. Proc. First Annual Field Screening Methods for Hazardous Waste Site Investigations, Las Vegas, NV, USEPA EPA/600/D-89/189.

REFERENCES (continued)

Oxenford, J.L., S.M. Klainer, T.M. Salinas, L. Todechiney, J.A. Kennedy, D.K. Dange, and K. Goswami, 1989, Development of a Fiber Optic Chemical Sensor for the Monitoring of Trichloroethylene in Drinking Water. SPIE Proceedings, Boston, MA, 108-114.

Plumb, R.H., Jr., 1992, The Importance of Volatile Organic Compounds as a Disposal Site Monitoring Parameter, in Lesage, S. and R.E. Jackson, eds., Groundwater Contamination and Analysis at Hazardous Waste Sites. Marcel Dekker, New York, NY, 173-197.

Plumb, R.H., Jr., 1991, The Occurrence of Appendix IX Organic Constituents in Disposal Site Ground Water, Ground Water Monitoring Review, 11 (2): 157-164.

Schabron, J.F. and J.F. Rovani, Jr., 1997, Practical Deviations from Henry's Law for Water/Air Partitioning of Volatile Organic Compounds, Proceedings of the 1997 USEPA/A&WMA International Symposium on Field Screening Methods for Hazardous Wastes and Toxic Chemicals, Air & Waste Management Association, 417-426.

Schabron, J.F., J.F. Rovani, Jr., and D.F. Moore, 1996, Down Hole Photoionization Detection of Volatile Organic Compounds, WRI Report 96-R003 to DOE under Cooperative Agreement DE-FC21-93MC30127.

Schabron, J.F., N.D. Niss, B.K. Hart, and S.S. Sorini, 1995, Remote Chemical Sensor Development: A New Field Screening Method for Soil Fuel Contamination. Laramie, WY, WRI Report WRI-95-R016.

Schabron, J.F., N.D. Niss, and B.K. Hart, 1991, Application and State of Development for Remote Chemical Sensors in Environmental Monitoring, a Literature Review, DOE Report DOE/MC/11076-3063.

Sorini, S.S. and J.F. Schabron, 1997, Development and Precision Testing of a Standard Test Method for Screening Fuels in Soils. *Journal of Testing and Evaluation, JTEVA*, Vol. 25, No. 4, pp. 400-405.

Stach, J., J. Flachowsky, M. Brodacki, and H.R. Doring, 1995, Field Screening for Volatile Organochlorine Compounds Using Ion Mobility Spectrometry, Field Screening Methods for Hazardous Wastes and Toxic Chemicals, Vol. 2, Conference Proceedings, Air & Waste Management Association, Pittsburgh, PA, 1046-1050.

REFERENCES (continued)

Stetter, R.S., and Z. Cao, 1990, Gas Sensor and Permeation Apparatus for the Determination of Chlorinated Hydrocarbons in Water, Analytical Chemistry, 62, 182-185.

U.S. Department of Energy Office of Industrial Technologies Report, 1998, "Petroleum Industry of the Future, Energy and Environmental Profile of the U.S. Petroleum Refining Industry," prepared by Energetics, Inc., Columbia, MD.

Walt, D.R, 1998, Fiber Optic Imaging Sensors, Accounts of Chemical Research, 31, 267-278.

Exhibit 2

WESTERN RESEARCH INSTITUTE

MUSTARD DOG™ VOLATILE CHEMICAL WARFARE AGENT DETECTOR

John F. Schabron
December 6, 2002
DRAFT

INTRODUCTION

Homeland Security Following the events of September 11, 2001, homeland security initiatives have assumed a high profile in the U.S. One ongoing concern is possible terrorist use of chemical warfare agents (CWAs). In 1994 the CWA Sarin was used by terrorists in the Tokyo subway system. Hundreds of people were affected and twelve died. The affected included many emergency response workers who did not know what they were dealing with (NRC 1999). Since many of the common volatile chemical warfare agents including Sarin, Phosgene, and Mustard Gases contain halogens, it appears possible that halogen-selective refrigerant leak detector sensors can be modified to rapidly detect a wide range of CWAs in air. Additional sensors could be assembled into an array along with the halogen-selective sensors to provide detection of non-halogenated CWAs. The proposed device is called the Mustard Dog™ CWA detector. Mustard Dog devices would be like smoke detectors in appearance and could be mounted on the walls of subways or buildings at a reasonable cost.

Refrigerant Leak Detectors as CWA Monitors Western Research Institute (WRI) is developing new portable field screening methodology (patent pending) under USDOE sponsorship to measure halogenated volatile organic compounds (VOCs) of environmental interest, such as tetrachloroethylene. Heated triode and corona discharge sensors are commonly used to detect leaks of refrigerants from air conditioners, freezers, and refrigerators. They are both selective to the presence of halogens. Detectors based on these technologies were modified to provide numerical output related to VOC concentration. Response profiles were developed for carbon tetrachloride and a variety of halogenated VOCs. The sensors were found not to respond to toluene or heptane vapors (aromatic and aliphatic fuel components). Response to water vapor is minimal. Results suggest the possibility of developing a system to detect halogen-containing volatile CWAs such as Sarin, Soman, Phosgene, and Mustard Gas in air. The devices could be used in combination with other existing universal VOC detection technologies to provide an array of sensors which could identify the type and amount of either halogenated or non-halogenated VOCs.

Related Research WRI has been actively involved in participation in ASTM Committee D-34 on Waste Management and the development and validation of new methods for environmental analysis. Recent accomplishments include development of a new UV-based method and portable test kit for measuring fuels in soils (Sorini and Schabron 1997, ASTM 2002a) (US Patents 5,561,065 and 5,976,883) and the Diesel Dog® soil test kit for fuel contamination in soil, which was awarded an American Chemical Society Industrial Innovations Award in 2001. WRI also developed ASTM D6418, Standard Practice for Using the Disposable En Core® Sampler for Sampling and Storing Soil for Volatile Organic Analysis, (ASTM 2002b) and is participating in revision and updating of ASTM D4547, Standard Guide for Sampling Waste and Soils for Volatile Organic Compounds (ASTM 2002c). WRI also has conducted research in the determination of VOCs by a variety of techniques, including photoionization detection (Schabron et al. 1991, Schabron and Rovani 1997).

REFRIGERANT LEAK DETECTORS AND ENVIRONMENTAL SCREENING

Two widely used commercially available refrigerant leak detectors are being evaluated for possible use as field screening and monitoring devices for halogenated VOCs, with the approval of the manufacturers. Heated triode leak monitors are available from Yokogowa U.S. Corporation in Newnan, GA. This technology was sold to Bacharach, Inc., New Kensington, PA in 2002. Corona discharge leak monitors are available from TIF Instruments, Inc., Mirimar, FL. Both types of sensor systems are able to detect leaks of down to about 0.1 to 0.5 ounce of refrigerant per year, and both selectively respond to the presence of halogens. With assistance from the manufacturers, WRI modified the devices to provide a numerical readout. Method development work is being performed with these devices (Schabron et al. 2002).

Results from the heated diode unit are read with a volt meter, and a frequency meter is used to obtain a numerical readout from the corona discharge sensor. Sensor response was evaluated with carbon tetrachloride and tetrachloroethylene (perchloroethylene, PCE), which represent halogenated VOCs with and without double bonds. The response characteristics were determined for the VOCs directly in headspace, without soil, in Tedlar bags. Detection limits were established at a S/N ratio of 10. The heated diode sensor can measure carbon tetrachloride in air down to levels of 0.2 vppm, with a linear response to higher levels. The corona discharge sensor can detect carbon tetrachloride to levels of about 10 vppm. This is comparable to PID detectors, which measure in the parts per million range. Potential interferences from volatile hydrocarbons, such as toluene and heptane, were evaluated and found to be nonexistent. The effect of humidity was also studied. Humidity did not change the response profiles, and small responses due to humidity could be zeroed out. Soil spiking experiments were also conducted. These showed that the VOCs measured in the headspace with the modified leak detectors could be used to screen halogenated VOC concentrations in soil. Using 100 g soil in 1L of headspace, detection limits in soil are estimated to be 10 - 50 ug/Kg (ppb). Response factors relative to carbon tetrachloride were obtained for a variety of halogenated VOCs. Some of the VOCs contained fluorine, bromine, and iodine so that the effects of the different halogens could be measured. Experiments are currently being performed.

CHEMICAL WARFARE AGENTS

Figure 25:
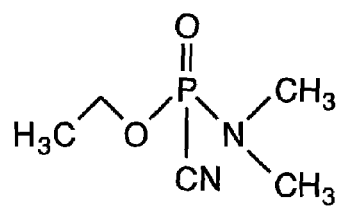
FIG. 25 is Nerve Agents
Figure 25:
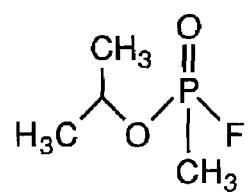
Figure 25:
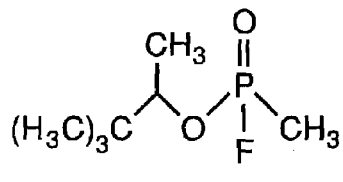
Figure 25:
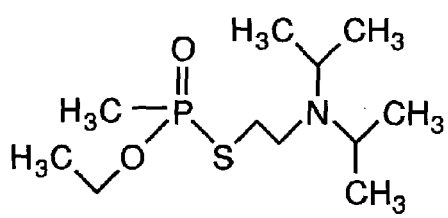

CWAs are chemicals that cause rapid death in very low doses These can be broadly divided into three main classes, although several other distinctions can be made (NRC 1999, Ellison 1999). These are the Nerve Agents, Blood Agents, and Blister Agents. Four common nerve agents, Sarin GB), Soman (GD), Tabun (GA), and VX are shown in Figure 25. These act as cholinesterase inhibitors and cause rapid death due to lack of nerve/muscular control. These are lethal variations of the familiar organophosphorous pesticides, parathion and malathion. The phosphate group is electronegative and it possibly can be detected by one or both of the halogen-selective sensors.

Figure 26:
FIG. 26 is Blood Agents
Figure 26:
Figure 27:
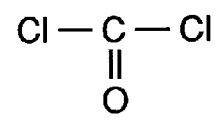
FIG. 27 is Vesicants, Blister Agents
Figure 27:
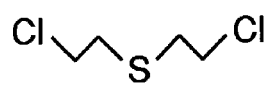
Figure 27:
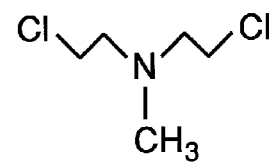

Two blood agents, Hydrogen Cyanide (AC) and Cyanogen Chloride (CK) are shown in Figure 26. These are cyanide delivery agents which inhibit cell respiration (use of oxygen), resulting in cell death. Five vesicants/blister agents Chlorine, Phosgene (CG), Sulfur Mustard (HD), Nitrogen Mustard, and Lewisite are shown in Figure 27. These cause burning, blisters, lung damage, and cell function failure. Of the above group, VX is not volatile and is delivered as an aerosol or adsorbed to fine particles.

LC 50 values for the chemical agents are shown in Table 4 (NIH 2002). The LC 50 is the concentration in air in vapor parts per million that will result in death to 50% of those exposed within a designated time frame, usually 10 minutes. Different numerical values are posted by different sources (Ellison 1999, NRC 1999), however the main point is that the lethal levels are in the low vppm levels. IDLH values (immediate danger to life and health) values are typically two to three orders of magnitude lower than LC 50 values. In use, CWAs would be deployed in values well above the LC 50, however the goal of any detection system or device is to sound the alarm as early as possible and at as low a level as possible. As discussed below, the detection technology presently used by U.S. troops requires liquid samples of the CWAs or takes a significant amount of time to obtain a result. These are essentially post-mortem detection technologies. Additional rapid, low cost, and sensitive approaches to CWA detection are needed The most widely used military detectors for CWAs in the field is the use of the so-called M8 and M9 indicator impregnated materials. These must be contacted with a liquid (very high level) sample before they respond. M8 coupons turn color in about one minute when exposed to liquid agent, from tan to green (V), yellow (G), or red (blister). Petroleum products can interfere. M9 tape turns color in about one minute when exposed to liquid, from green to red or pink. Petroleum products can interfere (Ellison 1999).

M-256 enzyme tickets take 15 minutes to respond to vapor by changing color (NRC 1999). M18 detector tubes require air to be drawn through different colorimetric tubes. The series of tests takes 24 minutes (Ellison 1999). Ion mobility spectroscopy (IMS) is used in expensive specialized instruments such as the CAM (chemical agent monitor), the ICAM (improved chemical agent monitor) and the M90. IMS devices are similar to the devices used in airports for screening wipe samples for explosives. These are used as post attack devices to sniff vapors from residual liquid contamination. There are a variety of potential interferences, including petroleum products (Ellison 1999).

A variety of other existing analytical techniques have been offered as CWA detectors. These include photoionization (PID), surface acoustic wave, and electrochemical sensors. These can respond to CWAs as well as other chemicals, and they might be useful in arrays of various detector types. Other more expensive and specialized approaches include portable infrared, gas chromatography, and gas chromatography/mass spectrometry systems.

REFERENCES

American Society for Testing and Materials, 2002a, D5831-96, Standard Test Method for Screening Fuels in Soils. *Annual Book of ASTM Standards*, Vol. 11.04, 329-337.

American Society for Testing and Materials, 2002b, D6418-01, Standard Practice for Using the Disposable En Core Sampler for Sampling and Storing Soil for Volatile Organic Analysis. *Annual Book of ASTM Standards*, Vol. 11.04, 580-592.

American Society for Testing and Materials, 2002c, D4547-98, Standard Guide for Sampling Waste and Soils for Volatile Organic Compounds. *Annual Book of ASTM Standards*, Vol. 11.04, 31-40.

Ellison, D.H., 1999, *Handbook of Chemical and Biological Warfare Agents*, CRC Press, Washington, D.C. ISBN 0-8493-280309

National Research Council (NRC), 1999, *Chemical and Biological Terrorism*, National Academy Press, Washington, D.C. ISBN 0-309-06195-4

National Institutes of Health (NIH) Toxnet, 2002, http://toxnet.nlm.nih.gov.

Schabron, J.F., N.D. Niss, and B.K. Hart, 1991, Application and State of Development for Remote Chemical Sensors in Environmental Monitoring, a Literature Review, DOE Report DOE/MC/11076-3063.

Schabron, J.F. and J.F. Rovani, Jr., 1997, Practical Deviations from Henry's Law for Water/Air Partitioning of Volatile Organic Compounds", Proceedings of the 1997 USEPA/A&WMA International Symposium on Field Screening Methods for Hazardous Wastes and Toxic Chemicals, Air & Waste Management Association, 417 - 426.

Schabron, J.F., J.F. Rovani, Jr., and T.M. Bomstad, 2002, Field Screening for Halogenated Volatile Organic Compounds, WRI Report 02-R013 to DOE under Cooperative Agreement DE-FC26-98FT40322.

Sorini, S.S. and J.F. Schabron, 1997, Development and Precision Testing of a Standard Test Method for Screening Fuels in Soils. *Journal of Testing and Evaluation, JTEVA*, Vol. 25, No. 4, pp. 400-405.

Table 4 CWA Vapor Lethal Levels

| Agent Type | Name | LC 50, vppm |
|---|---|---|
| Nerve | GA Tabun | 1 (10 min) |
| | GB Sarin | 1 (10 min) |
| | GD Soman | 1 (10 min) |
| | VX (Liquid) | Not volatile |
| Blood | AC Hydrogen Cyanide | 50 (30 min) |
| | CK Cyanogen Chloride | 0.3 (15 min) |
| Blister/Lung | Chlorine Gas | 10 (30 min) |
| | HD Sulfur Mustard | 10 (dog 10 min) |
| | HN Nitrogen Mustard | similar to HD |
| | Lewisite | 17 (10 min) |

What is claimed is:

1. A method of sensing an environmentally situated, non-refrigerant halogenated volatile compound comprising the steps of:
obtaining a refrigerant leak detector from which an electrical output can be obtained; and
establishing a numerical output provision element responsive to said electrical output for quantitatively displaying a value of a concentration of said environmentally situated, non-refrigerant halogenated volatile compound,
wherein said environmentally situated, non-refrigerant halogenated volatile compound is in an environmental area of interest.

2. A method of sensing an environmentally situated, non-refrigerant halogenated volatile compound as described in claim 1, wherein said step of establishing a numerical output provision element responsive to said electrical output for quantitatively displaying a value of a concentration of an environmentally situated, non-refrigerant halogenated volatile compound comprises the step of establishing a numerical output provision element responsive to said electrical output and that quantitatively displays a value of a concentration of a halogenated soil contaminant.

3. A method of sensing an environmentally situated, non-refrigerant halogenated volatile compound as describe in claim 1, wherein said step of establishing a numerical output provision element responsive to said electrical output for quantitatively displaying a value of a concentration of an environmentally situated, non-refrigerant halogenated volatile compound comprises the step of establishing a numerical output provision element that quantitatively displays a value of a concentration of an environmentally situated, non-refrigerant halogenated volatile compound in the presence of non-halogenated volatile compounds.

4. A method of sensing environmentally situated, non-refrigerant halogenated volatile compound as described in claim 1, wherein said step of establishing a numerical output provision element responsive to said electrical output and that quantitatively displays a value of a concentration of an environmentally situated, non-refrigerant halogenated volatile compound comprises the step of establishing a numeric output provision element responsive to said electrical output and that quantitatively displays a value of a concentration of a DNAPL that contaminate oil or water.

5. A method of sensing an environmentally situated, non-refrigerant halogenated volatile compound and described in claim 1, wherein said step of establishing a numerical output provision element responsive to said electrical output and that quantitatively displays a value of a concentration of an environmentally situated, non-refrigerant halogenated volatile compound comprises the step of establishing a numeric output provision element responsive to said electrical output and that quantitatively displays a value of a concentration of a halogenated volatile compound chemical warfare agent.

6. A method of sensing an environmently situated, non-refrigerant halogenated volatile compound as described claim 1, wherein said step of establishing a numerical output provision element responsive to said electrical output for quantitatively displaying a value a concentration of an environmentally situated, non-refrigerant halogenated volatile compound comprises the step of establishing a numeric output provision element responsive to said electrical output and that quantitatively displays a value of a concentration of said environmentally situated , non-refrigerant halogenated volatile compound.

7. A method of environmental monitoring for environmentally situated, halogenated volatile compounds comprising the steps of:
obtaining a refrigerant leak detector adapted to provide a value of a concentration of an environmentally situated, halogenated volatile compound;
establishing said refrigerant leak detector in an environmental area of interest; and
sensing said environmentally situated, halogenated volatile compound in said environmental area of interest by operating said refrigerant leak detector; and
quantitatively displaying said value of a concentration of said environmentally situated, halogenated volatile compound.

8. A method of environmental monitoring for environmentally situated, halogenated volatile compounds as described in claim 7, wherein said step of sensing an environmentally situated, halogenated volatile compound comprises the step of sensing halogenated contaminants.

9. A method of environmental monitoring for environmentally situated, halogenated volatile compounds as described in claim 7, wherein said step of obtaining a refrigerant leak detector comprises the step of obtaining a commercially available refrigerant leak detector.

10. A method of environmental monitoring for environmentally situated, halogenated volatile compounds as described in claim 7 or 9 wherein said step of obtaining a refrigerant leak detector comprises the step of obtaining a heated diode refrigerant leak detector.

11. A method of environmental monitoring for environmentally situated, halogenated volatile compounds as described in claim 7 or 9 wherein said step of obtaining a refrigerant leak detector comprises the step of obtaining a corona discharge refrigerant leak detector.

12. A method of environmental monitoring for environmentally situated, halogenated volatile compounds as described in claim 7, wherein said step of obtaining a refrigerant leak detector comprises the step of obtaining a refrigerant leak detector from which an electrical output can be obtained and further comprising the step of establishing a numerical output provision element responsive to said electrical output.

13. A method of environmental monitoring for environmentally situated, halogenated volatile compounds as described in claim 12, wherein said step of establishing a numerical output provision element responsive to said electrical output comprises the step of connecting a voltmeter in order to provide said numerical output.

14. A method of environmental monitoring for environmentally situated, halogenated volatile compounds as described in claim 12, wherein said step of establishing a numerical output provision element responsive to said electrical output comprises the step of connecting a frequency meter in order to provide said numerical output.

15. A method of environmental monitoring for environmentally situated, halogenated volatile compounds as described in claim 7, wherein said step of establishing said refrigerant leak detector in an environmental area of interest comprises the step of establishing said refrigerant leak detector in soil or in a headspace above soil.

16. A method of environmental monitoring for environmentally situated, halogenated volatile compounds as described in claim 7, wherein said step of sensing a halogenated volatile compound in said environmental area of interest by operating said refrigerant leak detector comprises the step of sensing a halogenated volatile chemical war agent selected from the group of a halogenated volatile chemical war agents consisting of: sarin, soman, cyanogen chloride, chlorine, phosgene, sulfur mustard, nitrogen mustard and lewisite.

17. A method of environmental monitoring for environmentally situated, halogenated volatile compounds as described in claim 7, further comprising the step of establishing an alert system responsive to said step of sensing a halogenated volatile compound in said environmental area of interest by operating said refrigerant leak detector.

18. A method of environmental monitoring for environmentally situated, halogenated volatile compounds as described in claim 7, wherein said step of sensing comprises in-field sensing of a halogenated volatile compound in soil, water or air.

19. A method of environmental monitoring for environmentally situated, halogenated volatile compounds as described in claim 7, wherein said step of establishing said refrigerant leak detector in an environmental area of interest comprises the step of establishing said refrigerant leak detector in a headspace above soil.

20. A method enviromnental monitoring for environmentally situated, halogenated volatile compounds as described in claim 7, wherein said step of establishing said refrigerant leak detector in an environmental area of interest comprises step of establishing said refrigerant leak detector in a headspace above water.

21. A method of environmental monitoring for environmentally situated, halogenated volatile compounds as described in claim 7, wherein said step of establishing said refrigerant leak detector in an environmental area of interest comprises the , step of establishing said refrigerant leak detector in air.

22. A method of environmental monitoring for environmentally situated, halogenated volatile compounds as described in claim 7, wherein said step of sensing said environmentally situated, halogenated volatile compound in said environmental at of interest by operating said refrigerant leak detector comprises the step sensing an environmentally situated, non-refrigerant halogenated volatile compound.

* * * * *